(12) United States Patent
Kling et al.

(10) Patent No.: US 8,233,954 B2
(45) Date of Patent: Jul. 31, 2012

(54) MUCOSAL SENSOR FOR THE ASSESSMENT OF TISSUE AND BLOOD CONSTITUENTS AND TECHNIQUE FOR USING THE SAME

(75) Inventors: Carl Kling, San Ramon, CA (US); Shannon Campbell, Oakland, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 1770 days.

(21) Appl. No.: 11/241,724

(22) Filed: Sep. 30, 2005

(65) Prior Publication Data

US 2007/0078318 A1  Apr. 5, 2007

(51) Int. Cl.
*A61B 5/1455* (2006.01)

(52) U.S. Cl. ............... 600/323; 600/309; 600/344

(58) Field of Classification Search ........... 600/309–344
See application file for complete search history.

(56) References Cited

U.S. PATENT DOCUMENTS

| | | |
|---|---|---|
| 3,518,313 A * | 6/1970 | Maruta et al. ............ 568/422 |
| 3,721,813 A | 3/1973 | Condon et al. |
| 4,586,513 A | 5/1986 | Hamaguri |
| 4,603,700 A | 8/1986 | Nichols et al. |
| 4,621,643 A | 11/1986 | New, Jr. et al. |
| 4,653,498 A | 3/1987 | New, Jr. et al. |
| 4,685,464 A | 8/1987 | Goldberger et al. |
| 4,694,833 A | 9/1987 | Hamaguri |
| 4,697,593 A | 10/1987 | Evans et al. |
| 4,700,708 A | 10/1987 | New, Jr. et al. |
| 4,714,080 A | 12/1987 | Edgar, Jr. et al. |
| 4,714,341 A | 12/1987 | Hamaguri et al. |
| 4,759,369 A | 7/1988 | Taylor |
| 4,770,179 A | 9/1988 | New, Jr. et al. |
| 4,773,422 A | 9/1988 | Isaacson et al. |
| 4,776,339 A | 10/1988 | Schreiber |
| 4,781,195 A | 11/1988 | Martin |
| 4,796,636 A | 1/1989 | Branstetter et al. |
| 4,800,495 A | 1/1989 | Smith |
| 4,800,885 A | 1/1989 | Johnson |
| 4,802,486 A | 2/1989 | Goodman et al. |
| 4,805,623 A | 2/1989 | Jöbsis |
| 4,807,630 A | 2/1989 | Malinouskas |
| 4,807,631 A | 2/1989 | Hersh et al. |
| 4,819,646 A | 4/1989 | Cheung et al. |
| 4,819,752 A | 4/1989 | Zelin |

(Continued)

FOREIGN PATENT DOCUMENTS

WO  WO 95/05416  2/1995

(Continued)

OTHER PUBLICATIONS

College of Pharmacy, Oregon State University and 3M Drug Delivery Systems; 3M Study Provides First Direct Comparison of Oral Controlled Release, Transdermal and Transmucosal Drug Delivery in Humans; article; pp. 10-12.

(Continued)

*Primary Examiner* — Eric Winakur
*Assistant Examiner* — Marjan Fardanesh
(74) *Attorney, Agent, or Firm* — Fletcher Yoder (57) ABSTRACT

A sensor for physiological constituent detection may be adapted to include a mucoadhesive. A sensor is provided that is appropriate for use on mucosal tissue. The mucoadhesive provides a mechanism for holding the sensor on the mucous membrane in order to measure physiological constituent levels in the tissue and blood.

9 Claims, 5 Drawing Sheets

U.S. PATENT DOCUMENTS

| | | |
|---|---|---|
| 4,824,242 A | 4/1989 | Frick et al. |
| 4,825,872 A | 5/1989 | Tan et al. |
| 4,825,879 A | 5/1989 | Tan et al. |
| 4,830,014 A | 5/1989 | Goodman et al. |
| 4,832,484 A | 5/1989 | Aoyagi et al. |
| 4,846,183 A | 7/1989 | Martin |
| 4,848,901 A | 7/1989 | Hood, Jr. |
| 4,854,699 A | 8/1989 | Edgar, Jr. |
| 4,859,056 A | 8/1989 | Prosser et al. |
| 4,859,057 A | 8/1989 | Taylor et al. |
| 4,863,265 A | 9/1989 | Flower et al. |
| 4,865,038 A | 9/1989 | Rich et al. |
| 4,867,557 A | 9/1989 | Takatani et al. |
| 4,869,253 A | 9/1989 | Craig, Jr. et al. |
| 4,869,254 A | 9/1989 | Stone et al. |
| 4,880,304 A | 11/1989 | Jaeb et al. |
| 4,883,055 A | 11/1989 | Merrick |
| 4,883,353 A | 11/1989 | Hausman et al. |
| 4,890,619 A | 1/1990 | Hatschek |
| 4,892,101 A | 1/1990 | Cheung et al. |
| 4,901,238 A | 2/1990 | Suzuki et al. |
| 4,908,762 A | 3/1990 | Suzuki et al. |
| 4,911,167 A | 3/1990 | Corenman et al. |
| 4,913,150 A | 4/1990 | Cheung et al. |
| 4,926,867 A | 5/1990 | Kanda et al. |
| 4,927,264 A | 5/1990 | Shiga et al. |
| 4,928,692 A | 5/1990 | Goodman et al. |
| 4,934,372 A | 6/1990 | Corenman et al. |
| 4,938,218 A | 7/1990 | Goodman et al. |
| 4,942,877 A | 7/1990 | Sakai et al. |
| 4,948,248 A | 8/1990 | Lehman |
| 4,955,379 A | 9/1990 | Hall |
| 4,960,126 A | 10/1990 | Conlon et al. |
| 4,964,408 A | 10/1990 | Hink et al. |
| 4,971,062 A | 11/1990 | Hasebe et al. |
| 4,974,591 A | 12/1990 | Awazu et al. |
| 5,007,423 A | 4/1991 | Branstetter et al. |
| 5,025,791 A | 6/1991 | Niwa |
| RE33,643 E | 7/1991 | Isaacson et al. |
| 5,028,787 A | 7/1991 | Rosenthal et al. |
| 5,035,243 A | 7/1991 | Muz |
| 5,040,539 A | 8/1991 | Hattori et al. |
| 5,054,488 A | 10/1991 | Muz |
| 5,055,671 A | 10/1991 | Jones |
| 5,058,588 A | 10/1991 | Kaestle |
| 5,065,749 A | 11/1991 | Hasebe et al. |
| 5,066,859 A | 11/1991 | Karkar et al. |
| 5,069,213 A | 12/1991 | Polczynksi |
| 5,078,136 A | 1/1992 | Stone et al. |
| 5,084,327 A | 1/1992 | Stengel |
| 5,088,493 A | 2/1992 | Giannini et al. |
| 5,090,410 A | 2/1992 | Saper et al. |
| 5,094,239 A | 3/1992 | Jaeb et al. |
| 5,094,240 A | 3/1992 | Muz |
| 5,099,841 A | 3/1992 | Heinonen et al. |
| 5,099,842 A | 3/1992 | Mannheimer et al. |
| H1039 H | 4/1992 | Tripp et al. |
| 5,104,623 A | 4/1992 | Miller |
| 5,109,849 A | 5/1992 | Goodman et al. |
| 5,111,817 A | 5/1992 | Clark et al. |
| 5,113,861 A | 5/1992 | Rother |
| 5,125,403 A | 6/1992 | Culp |
| 5,127,406 A | 7/1992 | Yamaguchi |
| 5,131,391 A | 7/1992 | Sakai et al. |
| 5,140,989 A | 8/1992 | Lewis et al. |
| 5,152,296 A | 10/1992 | Simons |
| 5,154,175 A | 10/1992 | Gunther |
| 5,158,082 A | 10/1992 | Jones |
| 5,170,786 A | 12/1992 | Thomas et al. |
| 5,188,108 A | 2/1993 | Secker et al. |
| 5,190,038 A | 3/1993 | Polson et al. |
| 5,193,542 A | 3/1993 | Missanelli et al. |
| 5,193,543 A | 3/1993 | Yelderman |
| 5,203,329 A | 4/1993 | Takatani et al. |
| 5,209,230 A | 5/1993 | Swedlow et al. |
| 5,213,099 A | 5/1993 | Tripp et al. |
| 5,216,598 A | 6/1993 | Branstetter et al. |
| 5,217,012 A | 6/1993 | Young et al. |
| 5,217,013 A | 6/1993 | Lewis et al. |
| 5,218,962 A | 6/1993 | Mannheimer et al. |
| 5,224,478 A | 7/1993 | Sakai et al. |
| 5,226,417 A | 7/1993 | Swedlow et al. |
| 5,228,440 A | 7/1993 | Chung et al. |
| 5,237,994 A | 8/1993 | Goldberger |
| 5,239,185 A | 8/1993 | Ito et al. |
| 5,246,002 A | 9/1993 | Prosser |
| 5,246,003 A | 9/1993 | DeLonzor |
| 5,247,931 A | 9/1993 | Norwood |
| 5,247,932 A | 9/1993 | Chung et al. |
| 5,249,576 A | 10/1993 | Goldberger et al. |
| 5,253,645 A | 10/1993 | Freidman et al. |
| 5,253,646 A | 10/1993 | Delpy et al. |
| 5,259,381 A | 11/1993 | Cheung et al. |
| 5,259,761 A | 11/1993 | Schnettler et al. |
| 5,263,244 A | 11/1993 | Centa et al. |
| 5,267,562 A | 12/1993 | Ukawa et al. |
| 5,267,563 A | 12/1993 | Swedlow et al. |
| 5,273,036 A | 12/1993 | Kronberg et al. |
| 5,275,159 A | 1/1994 | Griebel |
| 5,279,295 A | 1/1994 | Martens et al. |
| 5,285,783 A | 2/1994 | Secker |
| 5,285,784 A | 2/1994 | Seeker |
| 5,287,853 A | 2/1994 | Vester et al. |
| 5,291,884 A | 3/1994 | Heinemann et al. |
| 5,291,887 A | 3/1994 | Stanley et al. |
| 5,297,548 A | 3/1994 | Pologe |
| 5,299,120 A | 3/1994 | Kaestle |
| 5,299,570 A | 4/1994 | Hatschek |
| 5,309,908 A | 5/1994 | Freidman et al. |
| 5,311,865 A | 5/1994 | Mayeux |
| 5,313,940 A | 5/1994 | Fuse et al. |
| 5,323,776 A | 6/1994 | Blakely et al. |
| 5,329,922 A | 7/1994 | Atlee, III |
| 5,337,744 A | 8/1994 | Branigan |
| 5,339,810 A | 8/1994 | Ivers et al. |
| 5,343,818 A | 9/1994 | McCarthy et al. |
| 5,343,869 A | 9/1994 | Pross et al. |
| 5,348,003 A | 9/1994 | Caro |
| 5,348,004 A | 9/1994 | Hollub et al. |
| 5,349,519 A | 9/1994 | Kaestle |
| 5,349,952 A | 9/1994 | McCarthy et al. |
| 5,349,953 A | 9/1994 | McCarthy et al. |
| 5,351,685 A | 10/1994 | Potratz |
| 5,353,799 A | 10/1994 | Chance |
| 5,355,880 A | 10/1994 | Thomas et al. |
| 5,355,882 A | 10/1994 | Ukawa et al. |
| 5,361,758 A | 11/1994 | Hall et al. |
| 5,365,066 A | 11/1994 | Krueger, Jr. et al. |
| 5,368,025 A | 11/1994 | Young et al. |
| 5,368,026 A | 11/1994 | Swedlow et al. |
| 5,368,224 A | 11/1994 | Richardson et al. |
| 5,372,136 A | 12/1994 | Steuer et al. |
| 5,377,675 A | 1/1995 | Ruskewicz et al. |
| 5,385,143 A | 1/1995 | Aoyagi |
| 5,387,122 A | 2/1995 | Goldberger et al. |
| 5,390,670 A | 2/1995 | Centa et al. |
| 5,392,777 A | 2/1995 | Swedlow et al. |
| 5,398,680 A | 3/1995 | Polson et al. |
| 5,402,777 A | 4/1995 | Warring et al. |
| 5,411,023 A | 5/1995 | Morris, Sr. et al. |
| 5,411,024 A | 5/1995 | Thomas et al. |
| 5,413,099 A | 5/1995 | Schmidt et al. |
| 5,413,100 A | 5/1995 | Barthelemy et al. |
| 5,413,101 A | 5/1995 | Sugiura |
| 5,413,102 A | 5/1995 | Schmidt et al. |
| 5,417,207 A | 5/1995 | Young et al. |
| 5,421,329 A | 6/1995 | Casciani et al. |
| 5,425,360 A | 6/1995 | Nelson |
| 5,425,362 A | 6/1995 | Siker et al. |
| 5,427,093 A | 6/1995 | Ogawa et al. |
| 5,429,128 A | 7/1995 | Cadell et al. |
| 5,429,129 A | 7/1995 | Lovejoy et al. |
| 5,431,159 A | 7/1995 | Baker et al. |
| 5,431,170 A | 7/1995 | Mathews |
| 5,437,275 A | 8/1995 | Amundsen et al. |
| 5,438,986 A | 8/1995 | Disch et al. |
| 5,448,991 A | 9/1995 | Polson et al. |

| | | | | | | |
|---|---|---|---|---|---|---|
| 5,452,717 | A | 9/1995 | Branigan et al. | D393,830 | S | 4/1998 | Tobler et al. |
| 5,465,714 | A | 11/1995 | Scheuing | 5,743,260 | A | 4/1998 | Chung et al. |
| 5,469,845 | A | 11/1995 | DeLonzor et al. | 5,743,263 | A | 4/1998 | Baker, Jr. |
| RE35,122 | E | 12/1995 | Corenman et al. | 5,746,206 | A | 5/1998 | Mannheimer |
| 5,474,065 | A * | 12/1995 | Meathrel et al. ............ 600/376 | 5,746,697 | A | 5/1998 | Swedlow et al. |
| 5,482,034 | A | 1/1996 | Lewis et al. | 5,752,914 | A | 5/1998 | DeLonzor et al. |
| 5,482,036 | A | 1/1996 | Diab et al. | 5,755,226 | A | 5/1998 | Carim et al. |
| 5,483,646 | A | 1/1996 | Uchikoga | 5,758,644 | A | 6/1998 | Diab et al. |
| 5,485,847 | A | 1/1996 | Baker, Jr. | 5,760,910 | A | 6/1998 | Lepper, Jr. et al. |
| 5,490,505 | A | 2/1996 | Diab et al. | 5,766,125 | A | 6/1998 | Aoyagi et al. |
| 5,490,523 | A | 2/1996 | Isaacson et al. | 5,766,127 | A | 6/1998 | Pologe et al. |
| 5,491,299 | A | 2/1996 | Naylor et al. | 5,769,785 | A | 6/1998 | Diab et al. |
| 5,494,032 | A | 2/1996 | Robinson et al. | 5,772,587 | A | 6/1998 | Gratton et al. |
| 5,497,771 | A | 3/1996 | Rosenheimer | 5,774,213 | A | 6/1998 | Trebino et al. |
| 5,499,627 | A | 3/1996 | Steuer et al. | 5,776,058 | A | 7/1998 | Levinson et al. |
| 5,503,148 | A | 4/1996 | Pologe et al. | 5,776,059 | A | 7/1998 | Kaestle |
| 5,505,199 | A | 4/1996 | Kim | 5,779,630 | A | 7/1998 | Fein et al. |
| 5,507,286 | A | 4/1996 | Solenberger | 5,779,631 | A | 7/1998 | Chance |
| 5,511,546 | A | 4/1996 | Hon | 5,782,237 | A | 7/1998 | Casciani et al. |
| 5,517,988 | A | 5/1996 | Gerhard | 5,782,756 | A | 7/1998 | Mannheimer |
| 5,520,177 | A | 5/1996 | Ogawa et al. | 5,782,757 | A | 7/1998 | Diab et al. |
| 5,521,851 | A | 5/1996 | Wei et al. | 5,782,758 | A | 7/1998 | Ausec et al. |
| 5,522,388 | A | 6/1996 | Ishikawa et al. | 5,786,592 | A | 7/1998 | Hök |
| 5,524,617 | A | 6/1996 | Mannheimer | 5,790,729 | A | 8/1998 | Pologe et al. |
| 5,529,064 | A | 6/1996 | Rall et al. | 5,792,052 | A | 8/1998 | Isaacson et al. |
| 5,533,507 | A | 7/1996 | Potratz et al. | 5,795,292 | A | 8/1998 | Lewis et al. |
| 5,551,423 | A | 9/1996 | Sugiura | 5,795,304 | A | 8/1998 | Sun et al. |
| 5,551,424 | A | 9/1996 | Morrison et al. | 5,797,841 | A | 8/1998 | DeLonzor et al. |
| 5,553,614 | A | 9/1996 | Chance | 5,800,348 | A | 9/1998 | Kaestle |
| 5,553,615 | A | 9/1996 | Carim et al. | 5,800,349 | A | 9/1998 | Isaacson et al. |
| 5,555,882 | A | 9/1996 | Richardson et al. | 5,803,910 | A | 9/1998 | Potratz |
| 5,558,096 | A | 9/1996 | Palatnik | 5,807,246 | A | 9/1998 | Sakaguchi et al. |
| 5,560,355 | A | 10/1996 | Merchant et al. | 5,807,247 | A | 9/1998 | Merchant et al. |
| 5,564,417 | A | 10/1996 | Chance | 5,807,248 | A | 9/1998 | Mills |
| 5,575,284 | A | 11/1996 | Athan et al. | 5,810,723 | A | 9/1998 | Aldrich |
| 5,575,285 | A | 11/1996 | Takanashi et al. | 5,810,724 | A | 9/1998 | Gronvall |
| 5,577,500 | A | 11/1996 | Potratz | 5,813,980 | A | 9/1998 | Levinson et al. |
| 5,582,169 | A | 12/1996 | Oda et al. | 5,817,008 | A | 10/1998 | Rafert et al. |
| 5,584,296 | A | 12/1996 | Cui et al. | 5,817,009 | A | 10/1998 | Rosenheimer et al. |
| 5,588,425 | A | 12/1996 | Sackner et al. | 5,817,010 | A | 10/1998 | Hibl |
| 5,588,427 | A | 12/1996 | Tien | 5,818,985 | A | 10/1998 | Merchant et al. |
| 5,590,652 | A | 1/1997 | Inai | 5,820,550 | A | 10/1998 | Polson et al. |
| 5,595,176 | A | 1/1997 | Yamaura | 5,823,950 | A | 10/1998 | Diab et al. |
| 5,596,986 | A | 1/1997 | Goldfarb | 5,823,952 | A | 10/1998 | Levinson et al. |
| 5,611,337 | A | 3/1997 | Bukta | 5,827,182 | A | 10/1998 | Raley et al. |
| 5,617,852 | A | 4/1997 | MacGregor | 5,830,135 | A | 11/1998 | Bosque et al. |
| 5,626,140 | A | 5/1997 | Feldman et al. | 5,830,136 | A | 11/1998 | DeLonzor et al. |
| 5,629,992 | A | 5/1997 | Amersfoort et al. | 5,830,137 | A | 11/1998 | Scharf |
| 5,630,413 | A | 5/1997 | Thomas et al. | 5,839,439 | A | 11/1998 | Nierlich et al. |
| 5,632,272 | A | 5/1997 | Diab et al. | RE36,000 | E | 12/1998 | Swedlow et al. |
| 5,632,273 | A | 5/1997 | Suzuki | 5,842,979 | A | 12/1998 | Jarman et al. |
| 5,634,459 | A | 6/1997 | Gardosi | 5,842,981 | A | 12/1998 | Larsen et al. |
| 5,638,593 | A | 6/1997 | Gerhardt et al. | 5,842,982 | A | 12/1998 | Mannheimer |
| 5,638,818 | A | 6/1997 | Diab et al. | 5,846,190 | A | 12/1998 | Woehrle |
| 5,645,060 | A | 7/1997 | Yorkey et al. | 5,851,178 | A | 12/1998 | Aronow |
| 5,645,440 | A | 7/1997 | Tobler et al. | 5,851,179 | A * | 12/1998 | Ritson et al. .................. 600/338 |
| 5,660,567 | A | 8/1997 | Nierlich et al. | 5,853,364 | A | 12/1998 | Baker, Jr. et al. |
| 5,662,105 | A | 9/1997 | Tien | 5,860,919 | A | 1/1999 | Kiani-Azarbayjany et al. |
| 5,662,106 | A | 9/1997 | Swedlow et al. | 5,865,736 | A | 2/1999 | Baker, Jr. et al. |
| 5,665,477 | A | 9/1997 | Meathrel et al. | 5,871,442 | A | 2/1999 | Madarasz et al. |
| 5,666,952 | A | 9/1997 | Fuse et al. | 5,879,294 | A | 3/1999 | Anderson et al. |
| 5,671,529 | A | 9/1997 | Nelson | 5,885,213 | A | 3/1999 | Richardson et al. |
| 5,673,692 | A | 10/1997 | Schulze et al. | 5,890,929 | A | 4/1999 | Mills et al. |
| 5,673,693 | A | 10/1997 | Solenberger | 5,891,021 | A | 4/1999 | Dillon et al. |
| 5,676,139 | A | 10/1997 | Goldberger et al. | 5,891,022 | A | 4/1999 | Pologe |
| 5,676,141 | A | 10/1997 | Hollub | 5,891,024 | A | 4/1999 | Jarman et al. |
| 5,678,544 | A | 10/1997 | DeLonzor et al. | 5,891,025 | A | 4/1999 | Buschmann et al. |
| 5,680,857 | A | 10/1997 | Pelikan et al. | 5,891,026 | A | 4/1999 | Wang et al. |
| 5,685,299 | A | 11/1997 | Diab et al. | 5,902,235 | A | 5/1999 | Lewis et al. |
| 5,685,301 | A | 11/1997 | Klomhaus | 5,910,108 | A | 6/1999 | Solenberger |
| 5,687,719 | A | 11/1997 | Sato et al. | 5,911,690 | A | 6/1999 | Rall |
| 5,687,722 | A | 11/1997 | Tien et al. | 5,912,656 | A | 6/1999 | Tham et al. |
| 5,692,503 | A | 12/1997 | Kuenstner | 5,913,819 | A | 6/1999 | Taylor et al. |
| 5,692,505 | A | 12/1997 | Fouts | 5,916,154 | A | 6/1999 | Hobbs et al. |
| 5,709,205 | A | 1/1998 | Bukta | 5,916,155 | A | 6/1999 | Levinson et al. |
| 5,713,355 | A | 2/1998 | Richardson et al. | 5,919,133 | A | 7/1999 | Taylor et al. |
| 5,724,967 | A | 3/1998 | Venkatachalam | 5,919,134 | A | 7/1999 | Diab |
| 5,727,547 | A | 3/1998 | Levinson et al. | 5,920,263 | A | 7/1999 | Huttenhoff et al. |
| 5,731,582 | A | 3/1998 | West | 5,921,921 | A | 7/1999 | Potratz et al. |

| | | | | | | |
|---|---|---|---|---|---|---|
| 5,922,607 | A | 7/1999 | Bernreuter | 6,181,959 | B1 | 1/2001 | Schöllerman et al. |
| 5,924,979 | A | 7/1999 | Swedlow et al. | 6,184,521 | B1 | 2/2001 | Coffin, IV et al. |
| 5,924,980 | A | 7/1999 | Coetzee | 6,188,470 | B1 | 2/2001 | Grace |
| 5,924,982 | A | 7/1999 | Chin | 6,192,260 | B1 | 2/2001 | Chance |
| 5,924,985 | A | 7/1999 | Jones | 6,195,575 | B1 | 2/2001 | Levinson |
| 5,934,277 | A | 8/1999 | Mortz | 6,198,951 | B1 | 3/2001 | Kosuda et al. |
| 5,934,925 | A | 8/1999 | Tobler et al. | 6,206,830 | B1 | 3/2001 | Diab et al. |
| 5,940,182 | A | 8/1999 | Lepper, Jr. et al. | 6,213,952 | B1 | 4/2001 | Finarov et al. |
| 5,954,050 | A | 9/1999 | Christopher | 6,217,523 | B1 | 4/2001 | Amano et al. |
| 5,954,644 | A | 9/1999 | Dettling et al. | 6,222,189 | B1 | 4/2001 | Misner et al. |
| 5,960,610 | A | 10/1999 | Levinson et al. | 6,226,539 | B1 | 5/2001 | Potratz |
| 5,961,450 | A | 10/1999 | Merchant et al. | 6,226,540 | B1 | 5/2001 | Bernreuter et al. |
| 5,961,452 | A | 10/1999 | Chung et al. | 6,229,856 | B1 | 5/2001 | Diab et al. |
| 5,964,701 | A | 10/1999 | Asada et al. | 6,230,035 | B1 | 5/2001 | Aoyagi et al. |
| 5,971,930 | A | 10/1999 | Elghazzawi | 6,233,470 | B1 | 5/2001 | Tsuchiya |
| 5,978,691 | A | 11/1999 | Mills | 6,236,871 | B1 | 5/2001 | Tsuchiya |
| 5,978,693 | A | 11/1999 | Hamilton et al. | 6,236,872 | B1 | 5/2001 | Diab et al. |
| 5,983,122 | A | 11/1999 | Jarman et al. | 6,240,305 | B1 | 5/2001 | Tsuchiya |
| 5,987,343 | A | 11/1999 | Kinast | 6,253,097 | B1 | 6/2001 | Aronow et al. |
| 5,991,648 | A | 11/1999 | Levin | 6,253,098 | B1 | 6/2001 | Walker et al. |
| 5,995,855 | A | 11/1999 | Kiani et al. | 6,256,523 | B1 | 7/2001 | Diab et al. |
| 5,995,856 | A | 11/1999 | Mannheimer et al. | 6,256,524 | B1 | 7/2001 | Walker et al. |
| 5,995,858 | A | 11/1999 | Kinast | 6,261,236 | B1 | 7/2001 | Grimblatov |
| 5,995,859 | A | 11/1999 | Takahashi | 6,263,221 | B1 | 7/2001 | Chance et al. |
| 5,997,343 | A | 12/1999 | Mills et al. | 6,263,222 | B1 | 7/2001 | Diab et al. |
| 5,999,834 | A | 12/1999 | Wang et al. | 6,263,223 | B1 | 7/2001 | Shepherd et al. |
| 6,002,952 | A | 12/1999 | Diab et al. | 6,266,546 | B1 | 7/2001 | Steuer et al. |
| 6,005,658 | A | 12/1999 | Kaluza et al. | 6,266,547 | B1 | 7/2001 | Walker et al. |
| 6,006,120 | A | 12/1999 | Levin | 6,272,363 | B1 | 8/2001 | Casciani et al. |
| 6,011,985 | A | 1/2000 | Athan et al. | 6,278,522 | B1 | 8/2001 | Lepper, Jr. et al. |
| 6,011,986 | A | 1/2000 | Diab et al. | 6,280,213 | B1 | 8/2001 | Tobler et al. |
| 6,014,576 | A | 1/2000 | Raley et al. | 6,280,381 | B1 | 8/2001 | Malin et al. |
| 6,018,673 | A | 1/2000 | Chin et al. | 6,285,894 | B1 | 9/2001 | Oppelt et al. |
| 6,018,674 | A | 1/2000 | Aronow | 6,285,895 | B1 | 9/2001 | Ristolainen et al. |
| 6,022,321 | A | 2/2000 | Amano et al. | 6,285,896 | B1 | 9/2001 | Tobler et al. |
| 6,023,541 | A | 2/2000 | Merchant et al. | 6,285,897 | B1 | 9/2001 | Kilcoyne et al. |
| 6,026,312 | A | 2/2000 | Shemwell et al. | 6,298,252 | B1 | 10/2001 | Kovach et al. |
| 6,026,314 | A | 2/2000 | Amerov et al. | 6,308,089 | B1 | 10/2001 | Von der Ruhr et al. |
| 6,031,603 | A | 2/2000 | Fine et al. | 6,309,352 | B1 | 10/2001 | Oraevsky et al. |
| 6,035,223 | A | 3/2000 | Baker, Jr. | 6,321,100 | B1 | 11/2001 | Parker |
| 6,036,642 | A | 3/2000 | Diab et al. | 6,330,468 | B1 | 12/2001 | Scharf |
| 6,041,247 | A | 3/2000 | Weckstrom et al. | 6,334,065 | B1 | 12/2001 | Al-Ali et al. |
| 6,044,283 | A | 3/2000 | Fein et al. | 6,339,715 | B1 | 1/2002 | Bahr et al. |
| 6,047,201 | A | 4/2000 | Jackson, III | 6,343,223 | B1 | 1/2002 | Chin et al. |
| 6,061,584 | A | 5/2000 | Lovejoy et al. | 6,343,224 | B1 | 1/2002 | Parker |
| 6,064,898 | A | 5/2000 | Aldrich | 6,349,228 | B1 | 2/2002 | Kiani et al. |
| 6,064,899 | A | 5/2000 | Fein et al. | 6,351,658 | B1 | 2/2002 | Middleman et al. |
| 6,067,462 | A | 5/2000 | Diab et al. | 6,352,502 | B1 | 3/2002 | Chaiken et al. |
| 6,073,038 | A | 6/2000 | Wang et al. | 6,353,750 | B1 | 3/2002 | Kimura et al. |
| 6,078,833 | A | 6/2000 | Hueber | 6,356,774 | B1 | 3/2002 | Bernstein et al. |
| 6,081,735 | A | 6/2000 | Diab et al. | 6,360,113 | B1 | 3/2002 | Dettling |
| 6,081,742 | A | 6/2000 | Amano et al. | 6,360,114 | B1 | 3/2002 | Diab et al. |
| 6,083,157 | A | 7/2000 | Noller | 6,361,501 | B1 | 3/2002 | Amano et al. |
| 6,083,172 | A | 7/2000 | Baker, Jr. et al. | 6,363,269 | B1 | 3/2002 | Hanna et al. |
| 6,088,607 | A | 7/2000 | Diab et al. | 6,370,408 | B1 | 4/2002 | Merchant et al. |
| 6,094,592 | A | 7/2000 | Yorkey et al. | 6,370,409 | B1 | 4/2002 | Chung et al. |
| 6,095,974 | A | 8/2000 | Shemwell et al. | 6,374,129 | B1 | 4/2002 | Chin et al. |
| 6,104,938 | A | 8/2000 | Huiku et al. | 6,377,829 | B1 | 4/2002 | Al-Ali et al. |
| 6,112,107 | A | 8/2000 | Hannula | 6,381,479 | B1 | 4/2002 | Norris |
| 6,113,541 | A | 9/2000 | Dias et al. | 6,381,480 | B1 | 4/2002 | Stoddar et al. |
| 6,115,621 | A | 9/2000 | Chin | 6,385,471 | B1 | 5/2002 | Mortz |
| 6,122,535 | A | 9/2000 | Kaestle et al. | 6,385,821 | B1 | 5/2002 | Modgil et al. |
| 6,133,994 | A | 10/2000 | Mathews et al. | 6,388,240 | B2 | 5/2002 | Schulz et al. |
| 6,135,952 | A | 10/2000 | Coetzee | 6,393,310 | B1 | 5/2002 | Kuenster |
| 6,144,444 | A | 11/2000 | Haworth et al. | 6,397,091 | B2 | 5/2002 | Diab et al. |
| 6,144,867 | A | 11/2000 | Walker et al. | 6,397,092 | B1 | 5/2002 | Norris et al. |
| 6,144,868 | A | 11/2000 | Parker | 6,397,093 | B1 | 5/2002 | Aldrich |
| 6,149,481 | A | 11/2000 | Wang et al. | 6,400,971 | B1 | 6/2002 | Finarov et al. |
| 6,150,951 | A | 11/2000 | Olejniczak | 6,400,972 | B1 | 6/2002 | Fine |
| 6,151,107 | A | 11/2000 | Schöllerman et al. | 6,402,690 | B1 | 6/2002 | Rhee et al. |
| 6,151,518 | A | 11/2000 | Hayashi | 6,408,198 | B1 | 6/2002 | Hanna et al. |
| 6,152,754 | A | 11/2000 | Gerhardt et al. | 6,411,832 | B1 | 6/2002 | Guthermann |
| 6,154,667 | A | 11/2000 | Miura et al. | 6,411,833 | B1 | 6/2002 | Baker, Jr. et al. |
| 6,157,850 | A | 12/2000 | Diab et al. | 6,419,671 | B1 | 7/2002 | Lemberg |
| 6,163,715 | A | 12/2000 | Larsen et al. | 6,421,549 | B1 | 7/2002 | Jacques |
| 6,165,005 | A | 12/2000 | Mills et al. | 6,430,423 | B2 | 8/2002 | DeLonzor et al. |
| 6,173,196 | B1 | 1/2001 | Delonzor et al. | 6,430,513 | B1 | 8/2002 | Wang et al. |
| 6,178,343 | B1 | 1/2001 | Bindszus et al. | 6,430,525 | B1 | 8/2002 | Weber et al. |
| 6,181,958 | B1 | 1/2001 | Steuer et al. | 6,434,408 | B1 | 8/2002 | Heckel et al. |

| Patent | Type | Date | Inventor |
|---|---|---|---|
| 6,438,399 | B1 | 8/2002 | Kurth |
| 6,449,501 | B1 | 9/2002 | Reuss |
| 6,453,183 | B1 | 9/2002 | Walker |
| 6,453,184 | B1 | 9/2002 | Hyogo et al. |
| 6,456,862 | B2 | 9/2002 | Benni |
| 6,461,305 | B1 | 10/2002 | Schnall |
| 6,463,310 | B1 | 10/2002 | Swedlow et al. |
| 6,463,311 | B1 | 10/2002 | Diab |
| 6,466,808 | B1 | 10/2002 | Chin et al. |
| 6,466,809 | B1 | 10/2002 | Riley |
| 6,470,199 | B1 | 10/2002 | Kopotic et al. |
| 6,470,200 | B2 | 10/2002 | Walker et al. |
| 6,480,729 | B2 | 11/2002 | Stone |
| 6,490,466 | B1 | 12/2002 | Fein et al. |
| 6,496,711 | B1 | 12/2002 | Athan et al. |
| 6,498,942 | B1 | 12/2002 | Esenaliev et al. |
| 6,501,974 | B2 | 12/2002 | Huiku |
| 6,501,975 | B2 | 12/2002 | Diab et al. |
| 6,503,231 | B1 | 1/2003 | Prausnitz et al. |
| 6,505,060 | B1 | 1/2003 | Norris |
| 6,505,061 | B2 | 1/2003 | Larson |
| 6,505,133 | B1 | 1/2003 | Hanna et al. |
| 6,510,329 | B2 | 1/2003 | Heckel |
| 6,510,331 | B1 | 1/2003 | Williams et al. |
| 6,512,937 | B2 | 1/2003 | Blank et al. |
| 6,515,273 | B2 | 2/2003 | Al-Ali |
| 6,519,484 | B1 | 2/2003 | Lovejoy et al. |
| 6,519,486 | B1 | 2/2003 | Edgar, Jr. et al. |
| 6,519,487 | B1 | 2/2003 | Parker |
| 6,525,386 | B1 | 2/2003 | Mills et al. |
| 6,526,300 | B1 | 2/2003 | Kiani et al. |
| 6,526,301 | B2 | 2/2003 | Larsen et al. |
| 6,541,756 | B2 | 4/2003 | Schulz et al. |
| 6,542,764 | B1 | 4/2003 | Al-Ali et al. |
| 6,546,267 | B1 | 4/2003 | Sugiura et al. |
| 6,553,241 | B2 | 4/2003 | Mannheimer et al. |
| 6,553,242 | B1 | 4/2003 | Sarussi |
| 6,553,243 | B2 | 4/2003 | Gurley |
| 6,556,852 | B1 | 4/2003 | Schulze et al. |
| 6,560,470 | B1 | 5/2003 | Pologe |
| 6,564,077 | B2 | 5/2003 | Mortara |
| 6,564,088 | B1 | 5/2003 | Soller et al. |
| 6,571,113 | B1 | 5/2003 | Fein et al. |
| 6,571,114 | B1 | 5/2003 | Koike et al. |
| 6,574,491 | B2 | 6/2003 | Elghazzawi |
| 6,576,712 | B2 | 6/2003 | Feldstein et al. |
| 6,580,086 | B1 | 6/2003 | Schulz et al. |
| 6,584,336 | B1 | 6/2003 | Ali et al. |
| 6,587,703 | B2 | 7/2003 | Cheng et al. |
| 6,587,704 | B1 | 7/2003 | Fine et al. |
| 6,589,172 | B2 | 7/2003 | Williams et al. |
| 6,591,122 | B2 | 7/2003 | Schmitt |
| 6,591,123 | B2 | 7/2003 | Fein et al. |
| 6,594,511 | B2 | 7/2003 | Stone et al. |
| 6,594,512 | B2 | 7/2003 | Huang |
| 6,594,513 | B1 | 7/2003 | Jobsis et al. |
| 6,597,931 | B1 | 7/2003 | Cheng et al. |
| 6,597,933 | B2 | 7/2003 | Kiani et al. |
| 6,600,940 | B1 | 7/2003 | Fein et al. |
| 6,606,510 | B2 | 8/2003 | Swedlow et al. |
| 6,606,511 | B1 | 8/2003 | Ali et al. |
| 6,606,512 | B2 | 8/2003 | Muz et al. |
| 6,615,064 | B1 | 9/2003 | Aldrich |
| 6,615,065 | B1 | 9/2003 | Barrett et al. |
| 6,618,602 | B2 | 9/2003 | Levin et al. |
| 6,622,034 | B1 | 9/2003 | Gorski et al. |
| 6,628,975 | B1 | 9/2003 | Fein et al. |
| 6,631,281 | B1 | 10/2003 | Kästle |
| 6,643,530 | B2 | 11/2003 | Diab et al. |
| 6,643,531 | B1 | 11/2003 | Katarow |
| 6,647,279 | B2 | 11/2003 | Pologe |
| 6,647,280 | B2 | 11/2003 | Bahr et al. |
| 6,650,917 | B2 | 11/2003 | Diab et al. |
| 6,650,918 | B2 | 11/2003 | Terry |
| 6,654,621 | B2 | 11/2003 | Palatnik et al. |
| 6,654,622 | B1 | 11/2003 | Eberhard et al. |
| 6,654,623 | B1 | 11/2003 | Kästle |
| 6,654,624 | B2 | 11/2003 | Diab et al. |
| 6,658,276 | B2 | 12/2003 | Kianl et al. |
| 6,658,277 | B2 | 12/2003 | Wassermann |
| 6,662,033 | B2 | 12/2003 | Casciani et al. |
| 6,665,551 | B1 | 12/2003 | Suzuki |
| 6,668,182 | B2 | 12/2003 | Hubelbank |
| 6,668,183 | B2 | 12/2003 | Hicks et al. |
| 6,671,526 | B1 | 12/2003 | Aoyagi et al. |
| 6,671,528 | B2 | 12/2003 | Steuer et al. |
| 6,671,530 | B2 | 12/2003 | Chung et al. |
| 6,671,531 | B2 | 12/2003 | Al-Ali et al. |
| 6,671,532 | B1 | 12/2003 | Fudge et al. |
| 6,675,031 | B1 | 1/2004 | Porges et al. |
| 6,678,543 | B2 | 1/2004 | Diab et al. |
| 6,681,126 | B2 | 1/2004 | Solenberger |
| 6,681,128 | B2 | 1/2004 | Steuer et al. |
| 6,681,454 | B2 | 1/2004 | Modgil et al. |
| 6,684,090 | B2 | 1/2004 | Ali et al. |
| 6,684,091 | B2 | 1/2004 | Parker |
| 6,694,160 | B2 | 2/2004 | Chin |
| 6,697,653 | B2 | 2/2004 | Hanna |
| 6,697,655 | B2 | 2/2004 | Sueppel et al. |
| 6,697,656 | B1 | 2/2004 | Al-Ali |
| 6,697,658 | B2 | 2/2004 | Al-Ali |
| RE38,476 | E | 3/2004 | Diab et al. |
| 6,699,194 | B1 | 3/2004 | Diab et al. |
| 6,699,199 | B2 | 3/2004 | Asada et al. |
| 6,701,170 | B2 | 3/2004 | Stetson |
| 6,702,752 | B2 | 3/2004 | Dekker |
| 6,707,257 | B2 | 3/2004 | Norris |
| 6,708,049 | B1 | 3/2004 | Berson et al. |
| 6,709,402 | B2 | 3/2004 | Dekker |
| 6,711,424 | B1 | 3/2004 | Fine et al. |
| 6,711,425 | B1 | 3/2004 | Reuss |
| 6,711,426 | B2 | 3/2004 | Benaron et al. |
| 6,714,803 | B1 | 3/2004 | Mortz |
| 6,714,804 | B2 | 3/2004 | Al-Ali et al. |
| 6,714,805 | B2 | 3/2004 | Jeon et al. |
| RE38,492 | E | 4/2004 | Diab et al. |
| 6,719,686 | B2 | 4/2004 | Coakley et al. |
| 6,719,705 | B2 | 4/2004 | Mills |
| 6,720,734 | B2 | 4/2004 | Norris |
| 6,721,584 | B2 | 4/2004 | Baker, Jr. et al. |
| 6,721,585 | B1 | 4/2004 | Parker |
| 6,723,077 | B2 | 4/2004 | Pickup et al. |
| 6,725,074 | B1 | 4/2004 | Kästle |
| 6,725,075 | B2 | 4/2004 | Al-Ali |
| 6,731,963 | B2 | 5/2004 | Finarov et al. |
| 6,731,967 | B1 | 5/2004 | Turcott |
| 6,735,459 | B2 | 5/2004 | Parker |
| 6,745,060 | B2 | 6/2004 | Diab et al. |
| 6,745,061 | B1 | 6/2004 | Hicks et al. |
| 6,748,253 | B2 | 6/2004 | Norris et al. |
| 6,748,254 | B2 | 6/2004 | O'Neill et al. |
| 6,754,515 | B1 | 6/2004 | Pologe |
| 6,754,516 | B2 | 6/2004 | Mannheimer |
| 6,760,607 | B2 | 7/2004 | Al-Ali |
| 6,760,609 | B2 | 7/2004 | Jacques |
| 6,760,610 | B2 | 7/2004 | Tscupp et al. |
| 6,763,255 | B2 | 7/2004 | DeLonzor et al. |
| 6,763,256 | B2 | 7/2004 | Kimball et al. |
| 6,770,028 | B1 | 8/2004 | Ali et al. |
| 6,771,994 | B2 | 8/2004 | Kiani et al. |
| 6,773,397 | B2 | 8/2004 | Kelly |
| 6,778,923 | B2 | 8/2004 | Norris et al. |
| 6,780,158 | B2 | 8/2004 | Yarita |
| 6,791,689 | B1 | 9/2004 | Weckström |
| 6,792,300 | B1 | 9/2004 | Diab et al. |
| 6,793,654 | B2 | 9/2004 | Lemberg |
| 6,801,797 | B2 | 10/2004 | Mannheimer et al. |
| 6,801,798 | B2 | 10/2004 | Geddes et al. |
| 6,801,799 | B2 | 10/2004 | Mendelson |
| 6,801,802 | B2 | 10/2004 | Sitzman et al. |
| 6,802,812 | B1 | 10/2004 | Walker et al. |
| 6,805,673 | B2 | 10/2004 | Dekker |
| 6,810,277 | B2 | 10/2004 | Edgar, Jr. et al. |
| 6,813,511 | B2 | 11/2004 | Diab et al. |
| 6,816,266 | B2 | 11/2004 | Varshneya et al. |
| 6,816,741 | B2 | 11/2004 | Diab |
| 6,819,950 | B2 | 11/2004 | Mills |
| 6,822,564 | B2 | 11/2004 | Al-Ali |

| Patent No. | Date | Inventor |
|---|---|---|
| 6,825,619 B2 | 11/2004 | Norris |
| 6,826,419 B2 | 11/2004 | Diab et al. |
| 6,829,496 B2 | 12/2004 | Nagai et al. |
| 6,830,711 B2 | 12/2004 | Mills et al. |
| 6,836,679 B2 | 12/2004 | Baker, Jr. et al. |
| 6,839,579 B1 | 1/2005 | Chin |
| 6,839,580 B2 | 1/2005 | Zonios et al. |
| 6,839,582 B2 | 1/2005 | Heckel |
| 6,839,659 B2 | 1/2005 | Tarassenko et al. |
| 6,842,635 B1 | 1/2005 | Parker |
| 6,845,256 B2 | 1/2005 | Chin et al. |
| 6,850,787 B2 | 2/2005 | Weber et al. |
| 6,850,788 B2 | 2/2005 | Al-Ali |
| 6,850,789 B2 | 2/2005 | Schweitzer, Jr. et al. |
| 6,855,116 B2 | 2/2005 | Atlee |
| 6,861,639 B2 | 3/2005 | Al-Ali |
| 6,863,652 B2 | 3/2005 | Huang et al. |
| 6,865,407 B2 | 3/2005 | Kimball et al. |
| 6,869,402 B2 | 3/2005 | Arnold |
| 6,878,118 B2 | 4/2005 | Atlee |
| 6,879,850 B2 | 4/2005 | Kimball |
| 6,882,874 B2 | 4/2005 | Huiku |
| 6,889,153 B2 | 5/2005 | Dietiker |
| 6,898,452 B2 | 5/2005 | Al-Ali et al. |
| 6,909,912 B2 | 6/2005 | Melker et al. |
| 6,912,413 B2 | 6/2005 | Rantala et al. |
| 6,916,289 B2 | 7/2005 | Schnall |
| 6,920,345 B2 | 7/2005 | Al-Ali et al. |
| 6,931,269 B2 | 8/2005 | Terry |
| 6,934,570 B2 | 8/2005 | Kiani et al. |
| 6,939,307 B1 | 9/2005 | Dunlop |
| 6,941,162 B2 | 9/2005 | Fudge et al. |
| 6,947,781 B2 | 9/2005 | Asada et al. |
| 6,950,687 B2 | 9/2005 | Al-Ali |
| 6,961,600 B2 | 11/2005 | Kohl |
| 6,963,767 B2 | 11/2005 | Rantala et al. |
| 6,971,580 B2 | 12/2005 | Zhu et al. |
| 6,983,178 B2 | 1/2006 | Fine et al. |
| 6,985,763 B2 | 1/2006 | Boas et al. |
| 6,985,764 B2 | 1/2006 | Mason et al. |
| 6,990,426 B2 | 1/2006 | Yoon et al. |
| 6,992,751 B2 | 1/2006 | Okita et al. |
| 6,992,772 B2 | 1/2006 | Block et al. |
| 6,993,371 B2 | 1/2006 | Kiani et al. |
| 6,993,372 B2 | 1/2006 | Fine et al. |
| 6,996,427 B2 | 2/2006 | Ali et al. |
| 7,003,338 B2 | 2/2006 | Weber et al. |
| 7,003,339 B2 | 2/2006 | Diab et al. |
| 7,006,855 B1 | 2/2006 | Sarussi |
| 7,006,856 B2 | 2/2006 | Baker, Jr. et al. |
| 7,016,715 B2 | 3/2006 | Stetson |
| 7,020,507 B2 | 3/2006 | Scharf et al. |
| 7,024,233 B2 | 4/2006 | Ali et al. |
| 7,024,235 B2 | 4/2006 | Melker et al. |
| 7,025,728 B2 | 4/2006 | Ito et al. |
| 7,027,849 B2 | 4/2006 | Al-Ali et al. |
| 7,027,850 B2 | 4/2006 | Wasserman |
| 7,035,697 B1 | 4/2006 | Brown |
| 7,039,449 B2 | 5/2006 | Al-Ali |
| 7,043,289 B2 | 5/2006 | Fine et al. |
| 7,044,917 B2 | 5/2006 | Arnold |
| 7,047,055 B2 | 5/2006 | Boaz et al. |
| 7,047,056 B2 | 5/2006 | Hannula et al. |
| 7,060,035 B2 | 6/2006 | Wasserman et al. |
| 7,062,306 B2 | 6/2006 | Benaron et al. |
| 7,062,307 B2 | 6/2006 | Norris et al. |
| 7,067,893 B2 | 6/2006 | Mills et al. |
| 7,072,701 B2 | 7/2006 | Chen et al. |
| 7,072,702 B2 | 7/2006 | Edgar, Jr. et al. |
| 7,079,880 B2 | 7/2006 | Stetson |
| 7,085,597 B2 | 8/2006 | Fein et al. |
| 7,090,648 B2 | 8/2006 | Sackner et al. |
| 7,096,052 B2 | 8/2006 | Mason et al. |
| 7,096,054 B2 | 8/2006 | Abdul-Hafiz et al. |
| 7,103,402 B2 | 9/2006 | Vo-Dinh |
| 7,107,088 B2 | 9/2006 | Aceti |
| 7,113,815 B2 | 9/2006 | O'Neil et al. |
| 7,123,950 B2 | 10/2006 | Mannheimer |
| 7,127,278 B2 | 10/2006 | Melker et al. |
| 7,130,671 B2 | 10/2006 | Baker, Jr. et al. |
| 7,132,641 B2 | 11/2006 | Schulz et al. |
| 7,133,711 B2 | 11/2006 | Chernoguz et al. |
| 7,139,559 B2 | 11/2006 | Kenagy et al. |
| 7,142,901 B2 | 11/2006 | Kiani et al. |
| 7,173,525 B2 | 2/2007 | Albert |
| 7,190,987 B2 | 3/2007 | Lindekugel et al. |
| 7,198,778 B2 | 4/2007 | Achilefu et al. |
| 7,201,734 B2 | 4/2007 | Hickle |
| 7,209,775 B2 | 4/2007 | Bae et al. |
| 7,215,984 B2 | 5/2007 | Diab et al. |
| 7,225,006 B2 | 5/2007 | Al-Ali et al. |
| 7,236,811 B2 | 6/2007 | Schmitt |
| 7,236,881 B2 | 6/2007 | Liu et al. |
| 7,247,154 B2 | 7/2007 | Hickle |
| 7,248,910 B2 | 7/2007 | Li et al. |
| 7,254,433 B2 | 8/2007 | Diab et al. |
| 7,254,434 B2 | 8/2007 | Schulz et al. |
| 7,263,395 B2 | 8/2007 | Chan et al. |
| 7,272,426 B2 | 9/2007 | Scmid |
| 7,280,858 B2 | 10/2007 | Al-Ali et al. |
| 7,295,866 B2 | 11/2007 | Al-Ali et al. |
| 7,305,262 B2 | 12/2007 | Brodnick et al. |
| 7,315,753 B2 | 1/2008 | Baker, Jr. et al. |
| 7,330,746 B2 | 2/2008 | Demuth et al. |
| 7,438,687 B2 | 10/2008 | Lewicke |
| 2001/0021803 A1 | 9/2001 | Blank et al. |
| 2001/0051767 A1 | 12/2001 | Williams et al. |
| 2002/0026109 A1 | 2/2002 | Diab et al. |
| 2002/0028990 A1 | 3/2002 | Sheperd et al. |
| 2002/0038078 A1 | 3/2002 | Ito |
| 2002/0042558 A1 | 4/2002 | Mendelson |
| 2002/0068859 A1 | 6/2002 | Knopp |
| 2002/0095074 A1* | 7/2002 | Al-Ali .................. 600/310 |
| 2002/0128544 A1 | 9/2002 | Diab et al. |
| 2002/0133067 A1 | 9/2002 | Jackson, III |
| 2002/0156354 A1 | 10/2002 | Larson |
| 2002/0173706 A1 | 11/2002 | Takatani |
| 2002/0173709 A1 | 11/2002 | Fine et al. |
| 2002/0190863 A1 | 12/2002 | Lynn |
| 2002/0198442 A1 | 12/2002 | Rantala et al. |
| 2003/0018243 A1 | 1/2003 | Gerhardt et al. |
| 2003/0036690 A1 | 2/2003 | Geddes et al. |
| 2003/0045785 A1 | 3/2003 | Diab et al. |
| 2003/0073889 A1 | 4/2003 | Keilbach et al. |
| 2003/0073890 A1 | 4/2003 | Hanna |
| 2003/0100840 A1 | 5/2003 | Sugiura et al. |
| 2003/0132495 A1 | 7/2003 | Mills et al. |
| 2003/0135099 A1 | 7/2003 | Al-Ali |
| 2003/0162414 A1 | 8/2003 | Schulz et al. |
| 2003/0171662 A1 | 9/2003 | O'Connor et al. |
| 2003/0176776 A1 | 9/2003 | Huiku |
| 2003/0181797 A1 | 9/2003 | Kohl et al. |
| 2003/0181799 A1 | 9/2003 | Lindekugel et al. |
| 2003/0187337 A1 | 10/2003 | Tarassenko et al. |
| 2003/0195402 A1 | 10/2003 | Fein et al. |
| 2003/0197679 A1 | 10/2003 | Ali et al. |
| 2003/0212316 A1 | 11/2003 | Leiden et al. |
| 2003/0225323 A1 | 12/2003 | Kiani et al. |
| 2003/0225337 A1 | 12/2003 | Scharf et al. |
| 2003/0236452 A1 | 12/2003 | Melker et al. |
| 2003/0236647 A1 | 12/2003 | Yoon et al. |
| 2004/0006261 A1 | 1/2004 | Swedlow et al. |
| 2004/0010188 A1 | 1/2004 | Wasserman et al. |
| 2004/0024297 A1 | 2/2004 | Chen et al. |
| 2004/0024326 A1 | 2/2004 | Yeo et al. |
| 2004/0034293 A1 | 2/2004 | Kimball |
| 2004/0039272 A1 | 2/2004 | Abdul-Hafiz et al. |
| 2004/0039273 A1 | 2/2004 | Terry |
| 2004/0054269 A1 | 3/2004 | Rantala et al. |
| 2004/0054291 A1 | 3/2004 | Schulz et al. |
| 2004/0059209 A1 | 3/2004 | Al-Ali et al. |
| 2004/0059210 A1 | 3/2004 | Stetson |
| 2004/0064020 A1 | 4/2004 | Diab et al. |
| 2004/0068164 A1 | 4/2004 | Diab et al. |
| 2004/0087846 A1 | 5/2004 | Wasserman |
| 2004/0087916 A1 | 5/2004 | Pickup et al. |
| 2004/0092805 A1 | 5/2004 | Yarita |
| 2004/0097797 A1 | 5/2004 | Porges et al. |

| | | |
|---|---|---|
| 2004/0098009 A1 | 5/2004 | Boecker et al. |
| 2004/0107065 A1 | 6/2004 | Al-Ali et al. |
| 2004/0116788 A1 | 6/2004 | Chernoguz et al. |
| 2004/0116789 A1 | 6/2004 | Boaz et al. |
| 2004/0117891 A1 | 6/2004 | Hannula et al. |
| 2004/0122300 A1 | 6/2004 | Boas et al. |
| 2004/0122302 A1 | 6/2004 | Mason et al. |
| 2004/0133087 A1 | 7/2004 | Ali et al. |
| 2004/0133088 A1 | 7/2004 | Al-Ali et al. |
| 2004/0138538 A1 | 7/2004 | Stetson |
| 2004/0138540 A1 | 7/2004 | Baker, Jr. et al. |
| 2004/0143172 A1 | 7/2004 | Fudge et al. |
| 2004/0147821 A1 | 7/2004 | Al-Ali et al. |
| 2004/0147822 A1 | 7/2004 | Al-Ali et al. |
| 2004/0147823 A1 | 7/2004 | Kiani et al. |
| 2004/0147824 A1 | 7/2004 | Diab et al. |
| 2004/0152965 A1 | 8/2004 | Diab et al. |
| 2004/0158134 A1 | 8/2004 | Diab et al. |
| 2004/0158135 A1 | 8/2004 | Baker, Jr. et al. |
| 2004/0162472 A1 | 8/2004 | Berson et al. |
| 2004/0171920 A1 | 9/2004 | Mannheimer et al. |
| 2004/0171948 A1 | 9/2004 | Terry |
| 2004/0176671 A1 | 9/2004 | Fine et al. |
| 2004/0181133 A1 | 9/2004 | Al-Ali et al. |
| 2004/0181134 A1 | 9/2004 | Baker, Jr. et al. |
| 2004/0181196 A1 | 9/2004 | Pickup et al. |
| 2004/0186358 A1 | 9/2004 | Chernow et al. |
| 2004/0199063 A1 | 10/2004 | O'Neil et al. |
| 2004/0204636 A1 | 10/2004 | Diab et al. |
| 2004/0204637 A1 | 10/2004 | Diab et al. |
| 2004/0204638 A1 | 10/2004 | Diab et al. |
| 2004/0204639 A1 | 10/2004 | Casciani et al. |
| 2004/0204865 A1 | 10/2004 | Lee et al. |
| 2004/0210146 A1 | 10/2004 | Diab et al. |
| 2004/0215069 A1 | 10/2004 | Mannheimer |
| 2004/0230107 A1 | 11/2004 | Asada et al. |
| 2004/0230108 A1 | 11/2004 | Melker et al. |
| 2004/0236196 A1 | 11/2004 | Diab et al. |
| 2004/0242980 A1 | 12/2004 | Kiani et al. |
| 2004/0249252 A1 | 12/2004 | Fine et al. |
| 2004/0257557 A1 | 12/2004 | Block et al. |
| 2004/0260161 A1 | 12/2004 | Melker et al. |
| 2004/0267103 A1 | 12/2004 | Li et al. |
| 2004/0267104 A1 | 12/2004 | Hannula et al. |
| 2004/0267140 A1 | 12/2004 | Ito et al. |
| 2005/0004479 A1 | 1/2005 | Townsend et al. |
| 2005/0010092 A1 | 1/2005 | Weber et al. |
| 2005/0020887 A1 | 1/2005 | Goldberg |
| 2005/0020894 A1 | 1/2005 | Norris et al. |
| 2005/0033128 A1 | 2/2005 | Ali et al. |
| 2005/0033129 A1 | 2/2005 | Edgar, Jr. et al. |
| 2005/0043599 A1 | 2/2005 | O'Mara |
| 2005/0043600 A1 | 2/2005 | Diab et al. |
| 2005/0049470 A1 | 3/2005 | Terry |
| 2005/0049471 A1 | 3/2005 | Aceti |
| 2005/0075550 A1 | 4/2005 | Lindekugel |
| 2005/0113651 A1 | 5/2005 | Wood et al. |
| 2005/0177034 A1 | 8/2005 | Beaumont |
| 2005/0182389 A1 | 8/2005 | Laporte et al. |
| 2005/0197548 A1 | 9/2005 | Dietiker |
| 2005/0228248 A1 | 10/2005 | Dietiker |
| 2005/0277819 A1 | 12/2005 | Kiani et al. |
| 2005/0283059 A1 | 12/2005 | Iyer et al. |
| 2006/0020179 A1 | 1/2006 | Anderson et al. |
| 2006/0036137 A1 | 2/2006 | Lewicke |
| 2006/0047190 A1* | 3/2006 | Jenkins et al. ............ 600/340 |
| 2006/0058594 A1 | 3/2006 | Ishizuka et al. |
| 2006/0084852 A1 | 4/2006 | Mason et al. |
| 2006/0089547 A1 | 4/2006 | Sarussi |
| 2006/0106294 A1 | 5/2006 | Maser et al. |
| 2006/0189872 A1 | 8/2006 | Arnold |
| 2006/0195028 A1 | 8/2006 | Hannula et al. |
| 2006/0224058 A1 | 10/2006 | Mannheimer |
| 2006/0247501 A1 | 11/2006 | Ali |
| 2006/0258921 A1 | 11/2006 | Addison et al. |
| 2006/0258952 A1 | 11/2006 | Stahmann et al. |
| 2006/0276697 A1 | 12/2006 | Demuth et al. |
| 2006/0276700 A1 | 12/2006 | O'Neil |
| 2007/0027375 A1 | 2/2007 | Melker et al. |
| 2007/0032710 A1 | 2/2007 | Raridan et al. |
| 2007/0032712 A1 | 2/2007 | Raridan et al. |
| 2007/0032715 A1 | 2/2007 | Eghbal et al. |
| 2007/0038126 A1 | 2/2007 | Pyle et al. |
| 2007/0073121 A1 | 3/2007 | Hoarau et al. |
| 2007/0073125 A1 | 3/2007 | Hoarau et al. |
| 2007/0073126 A1 | 3/2007 | Raridan, Jr. |
| 2007/0073128 A1 | 3/2007 | Hoarau et al. |
| 2008/0009689 A1 | 1/2008 | Benaron et al. |
| 2008/0021379 A1 | 1/2008 | Hickle |
| 2008/0188727 A1 | 8/2008 | Benaron et al. |
| 2008/0287758 A1 | 11/2008 | Benaron et al. |

FOREIGN PATENT DOCUMENTS

| | | |
|---|---|---|
| WO | WO 98/15223 | 4/1998 |
| WO | WO9851212 | 11/1998 |
| WO | WO 99/16346 | 4/1999 |
| WO | WO0117421 | 3/2001 |
| WO | WO 2006/094513 A2 | 9/2006 |

OTHER PUBLICATIONS

Pharmaceutical Polymers; Bulletin 16; entitled "Biodhesion"; 18 pages.

Michael J Rathbone et al.; entitled "Modified-Release Drug Delivery Technology"; web page http://www.chipsbooks.com/modrug.htm; printed Sep. 28, 2004; 3 pages.

Article entitled "STRIANT (testosterone buccal system) mucoadhesive"; web page http://www.columbialabs.com/Striant/Striant_Full_Prescribing_info.htm; printed Oct. 6, 2004; 5 pages.

Ingenta: article summary entitled Mucoadhesive and Penetration Enhancement Properties of Three Grades of Hyaluronic Acid Using Porcine Buccal and Vaginal Tissue, Caco-2 Cell Lines, a Rat Jejunum; Journal of Pharmacy and Pharmacology; Sep. 1, 2004; vol. 56, No. 9, 1083-1090(8); from webpage http://www.ingenta.com/isis/searching/Expand/ingenta?pub=infobike;//rpsgb/jpp/2004/000... on Oct. 6, 2004; 1 page.

Web article; entitled Opportunities, Mucoadhesive Erodible Disc (OraDisc); Pharmalicensing.com; http://pharmalicensing.com/licensing/displicopp/2316 printed on Sep. 28, 2004; 2 pages.

Nicholas A. Peppas; article entitled Nanoscale Technology of Mucoadhesive Interactions; Advanced Drug Delivery Reviews 56 (2004) 1675-1687; 13 pages.

Lev Bromberg; article entitled Biadhesive properties and rheology of polyether-modified poly(acrylic acid) hydrogels; Elsevier, international journal of pharmaceutics; 16 pages.

Sanju Dhawan; article entitled: "Evaluation of Mucoadhesive Properties of Chitosan Microspheres Prepared by Different Methods"; web page http://www.aapspharmscitch.org/view.asp?art=pt050467& pdf=yes; 13 pages.

Juan Manuel Llabot; article entitled: "Double-Layered Mucoadhesive Tablets Containing Nystatin"; Submitted: Mar. 11, 2002; AAPS PharmSciTech 2002; 3 (3) article 22 (http://www.aapspharmsci.org) 6 pages.

Edith Mathiowitz et al.; article entitled "Bioadhesive Drug Delivery Systems: Fundamentals, Novel Approaches and Development"; website http://www.chipsbooks.com/bioadhes.htm; printed out on Sep. 28, 2004; 3 pages.

Sanju Dhawan; article entitled Evaluation of Mucoadhesive Properties of Chitosan Microspheres Prepared by Different Methods; Submitted: May 17, 2004; AAPS PharmSciTech 2004; 5 (4) Article 57 (http://www.aapspharmscitech.org). 7 pages.

Article entitled "A comparison of TMD Matrix and Reservoir Configurations"; 1 page.

Webpage article entitled "Columbia Laboratories, Inc."; http://www.columbialabs.com/AboutUs.htm; 1 page.

Website article entitled "Our Bioadhesive Gel"; http:www.prochieve8.com/bioadhesive/default.aspx; 2 pages.

Website article entitled "Technology Portfolio"; http://www.accesspharma.com/products/index.html; 10 pages.

Website article entitled STRIANT (Testosterone Buccal System) Mucoadhesive CIII; http;//www.columbialabs.com/Striant/Striant_Fact_Sheet.htm; 3 pages.

Drug insert pamplet for STRIANT (testosterone buccal system) 2 pages.

* cited by examiner

MUCOSAL SENSOR FOR THE ASSESSMENT OF TISSUE AND BLOOD CONSTITUENTS AND TECHNIQUE FOR USING THE SAME

BACKGROUND OF THE INVENTION

1. Field of the Invention

The present invention relates generally to medical devices and, more particularly, to sensors placed on a mucosal surface used for sensing physiological parameters of a patient.

2. Description of the Related Art

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring many such characteristics of a patient. Such devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, for example the blood-oxygen saturation of hemoglobin in arterial blood, the volume of individual blood pulsations supplying the tissue, and/or the rate of blood pulsations corresponding to each heartbeat of a patient. In fact, the "pulse" in pulse oximetry refers to the time varying amount of arterial blood in the tissue during different phases of the cardiac cycle.

Pulse oximeters typically utilize a non-invasive sensor that transmits electromagnetic radiation, for example light, through a patient's tissue and that photoelectrically detects the absorption and scattering of the transmitted light in such tissue. One or more of the above physiological characteristics may then be calculated based upon the amount of light absorbed and scattered. More specifically, the light passed through the tissue is typically selected to be of one or more wavelengths that may be absorbed and scattered by the blood in an amount correlative to the amount of the blood constituent present in the tissue. The measured amount of light absorbed and scattered may then be used to estimate the amount of blood constituent in the tissue using various algorithms.

Pulse oximetry is sensitive to movement, and various types of motion may cause artifacts that may obscure the blood constituent signal. For example, motion artifacts may be caused by moving a sensor in relation to the tissue, by increasing or decreasing the physical distance between emitters and detectors in a sensor, by changing the direction of emitters or detectors with respect to tissue or each other, by changing the angles of incidence and interfaces probed by the light, by directing the optical path through different amounts or types of tissue, or by expanding, compressing or otherwise altering tissue near a sensor. In the emergency room, critical care, intensive care, and trauma center settings, where pulse oximetry is commonly used for patient monitoring, the wide variety of sources of motion artifacts includes moving of a patient or the sensor by healthcare workers, physical motion of an unanaesthetised or ambulatory patient, shivering, seizures, agitation, response to pain and loss of neural control. These motions oftentimes have similar frequency content to the pulse, and may lead to similar or even larger optical modulations than the pulse. Thus, it is desirable to reduce the movement of a pulse oximetry sensor in order to mitigate artifacts. Use of a mucoadhesive may urge the sensor into better contact with the desired site of measurement and may eliminate or reduce motion of the sensor relative to the tissue.

Alternative means of monitoring tissue constituents may also be of clinical interest. One such parameter of interest is carbon dioxide. Elevated levels of carbon dioxide in the tissue may be related to poor perfusion. Thus, assessment of carbon dioxide levels may be useful for diagnosing a variety of clinical states related to poor perfusion. One method of determining the level of blood carbon dioxide involves measuring carbon dioxide levels of respiratory gases. In relatively healthy individuals, the carbon dioxide in the bloodstream equilibrates rapidly with carbon dioxide in the lungs, the partial pressure of the carbon dioxide in the lungs approaches the amount in the blood during each breath. Accordingly, physicians often monitor respiratory gases at the end of expiration in order to estimate the carbon dioxide levels in the blood.

Respiratory gas analyzers typically function by passing electromagnetic radiation through a respiratory gas sample and measuring the absorption that is related to carbon dioxide. Often, the gas samples are collected with adapters that are fitted into patients being given respiratory assistance, for example patients under anesthesia, or patients on life support systems, to connect between the endotracheal tube (ET tube) and the ventilating tube of the breathing apparatus. These tubes convey respiratory gases to the patient and exhaled breath away from the patient. The airway adapter is in the form of a short connector of tubular shape, and is required to make a connection between the generally very different cross sections of these two tubes. Respiratory gases may also be collected through the use of cannulas, which are flexible tubes that are threaded through the mouth or nose. Respiratory gas samples collected from a cannula may be aspirated from the airway stream and exposed to a carbon dioxide sensor.

It is often inconvenient to measure carbon dioxide in respiratory gases from respiratory gas samples collected from an intubation tube or cannula. Although these methods are considered to be noninvasive, as the surface of the skin is not breached, the insertion of such devices may cause discomfort for the patient. Further, the insertion and operation of such devices also involves the assistance of skilled medical personnel.

Carbon dioxide and other physiological parameters may also be measured transcutaneously by sensors held against a patient's skin. Transcutaneously measured carbon dioxide may also be clinically useful when compared to carbon dioxide measured in respiratory gases. For example, variations in carbon dioxide measurements between these two methods may be diagnostic for certain clinical states. While transcutaneous sensors may be easier to use than respiratory gas sensors, they also have certain disadvantages. As transcutaneous sensors depend upon the perfusion of carbon dioxide through a relatively thick epidermal layer, these sensors may not be as accurate.

Direct measurement of tissue carbon dioxide, particularly in tissues sensitive to hypoperfusion, provides clinicians with important diagnostic information regarding systemic circulation and/or onset of septic shock. The oral mucosa is a tissue involved in the visceral response to systemic hypoperfusion.

A sensor held in position on the oral mucosa could provide trending information about a patient's level of systemic perfusion.

SUMMARY

Certain aspects commensurate in scope with the originally claimed invention are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

There is provided a sensor that includes: an indicator adapted to provide feedback related to a physiological constituent; and a mucoadhesive disposed on a tissue-contacting side of the sensor.

There is also provided a system that includes a sensor adapted to be operatively coupled to the monitor. The sensor includes: an indicator adapted to provide feedback related to a physiological constituent; and a mucoadhesive disposed on a tissue-contacting side of the sensor.

There is also provided a method of operating a sensor that includes: securing a sensor to a mucosal tissue with a mucoadhesive, wherein the sensor is adapted to provide feedback related to a physiological constituent.

There is also provided a method of manufacturing a sensor that includes: providing an indicator adapted to provide feedback related to a physiological constituent; and providing a mucoadhesive disposed on a tissue-contacting side of the sensor.

BRIEF DESCRIPTION OF THE DRAWINGS

Advantages of the invention may become apparent upon reading the following detailed description and upon reference to the drawings in which.

DETAILED DESCRIPTION OF SPECIFIC EMBODIMENTS

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, for example compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Sensors are provided herein that may assess the presence of physiological constituents while secured to the mucosal tissue by mucoadhesives, which provide multiple advantages. A secure mounting of the sensor to the mucosal tissue with mucoadhesives reduces movement of the sensor, which may cause signal artifacts. A sensor may be attached to mucosal tissue that is easily accessible to a healthcare worker, for example buccal tissue, which does not involve the insertion of respiratory airway tubes that may cause patient discomfort. Mucoadhesive mounting of sensors to the mucous membrane helps seal the sensor to the tissue, thus preventing tissue constituents at the sensor site from diffusing away before reaching the sensing elements of the sensor. Conversely, use of a mucoadhesive prevents oral fluids or respiratory gases from contaminating the sensor site. The term mucoadhesive refers to a substance that sticks to or adheres to the mucous membrane by any number of mechanisms, for example, but not limited to the following: hydrogen-bonding, ionic interaction, hydrophobic interaction, van der Waals interaction, or combinations thereof.

Generally, it is envisioned that a sensor according to the present technique is appropriate for use in determining the presence or levels of physiological constituents, including blood and tissue parameters. For example, carbon dioxide or other constituents may be assessed by utilization of a sensor placed directly on the mucosal surface. Thus, clinically relevant information may be ascertained and utilized for diagnostic purposes, e.g. poor tissue perfusion.

The sensor is secured to the mucosal tissue with a mucoadhesive, forming a seal to prevent the blood or tissue constituents, for example carbon dioxide, from diffusing away. Additionally, the seal prevents movement of the sensor from altering the optical path of any spectrophotometric elements of the sensor, which may result in signal interference. The sensor may be used in the oral and nasal passages. The oral passages may include the floor of the mouth, the roof of the mouth, the soft palate, the cheeks, the gums, the lips, and any other oral tissue. Further, a sensor as described herein is appropriate for use adjacent to or proximate to any mucosal surface, i.e. patient surfaces that include a mucous membrane or surfaces that are associated with mucus production. In addition to the oral and nasal mucosa, mucosal surfaces may include respiratory, gastrointestinal or urogenital surfaces.

Sensors as provided by the present techniques may be disposable or reusable. In addition, the sensors may be appropriate for short-term (e.g. minutes) or long-term (e.g. hours, days, or longer) monitoring. In addition to carbon dioxide monitoring, sensors as provided herein may be used to monitor oxygen, ethanol, metabolic trace gases, e.g. acetone or anesthetic gases, e.g. isoflurane, halothane, desflurane, sevoflurane and enflurane that may diffuse transcutaneously. Additionally, sensors as provided herein may be useful for monitoring tissue metabolites, e.g. cytochrome a/a3, phosphomonoesters, $H^+$, ATP, ADP, NADH, $NAD^+$, cytokines, and inflammatory markers. Further, sensors as provided herein are appropriate for use in determination of blood oxygen saturation as well as measurement and/or analysis of other blood and/or tissue constituents using principles of pulse oximetry. For example, the present techniques may be utilized for the measurement and/or analysis of carboxyhemoglobin, methemoglobin, total hemoglobin, fractional hemoglobin, intravascular dyes, and/or water content.

Figure 1:
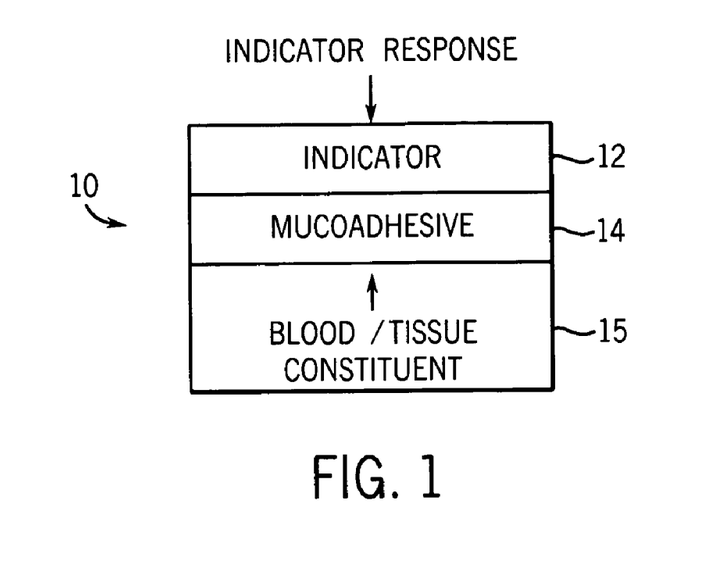
FIG. 1 is a schematic cross-section of a sensor showing a mucoadhesive layer according to the present invention.

FIG. 1 is a schematic view of an exemplary sensor 10 according to the present techniques. The sensor 10 has an indicator layer 12 and a mucoadhesive layer 14. When the sensor 10 is contacted with a tissue or fluid sensor site, the mucoadhesive layer 14 forms an adhesion complex with the tissue. When the sensor 10 is adhered to the mucous membrane, physiological constituents, for example blood oxygen, may be spectrophotometrically assessed, as discussed in more detail herein. In such an embodiment, the indicator layer 12 may include an emitter and detector pair. Alternatively, tissue gases for example carbon dioxide may perfuse through the mucoadhesive-tissue complex into the indicator layer 12. The indicator layer 12 may be adapted to respond to the presence of carbon dioxide, and provides a feedback, discussed in more detail below.

The mucoadhesive layer 14 may include a variety of mucoadhesive compositions to secure a sensor to mucosal tissue according to the present techniques. Suitable mucoadhesives include, but are not limited to hydroxypropyl cellulose, hydroxypropyl methylcellulose, hydroxyethylcellulose, ethylcellulose, carboxymethylcellulose, dextran, guar gum, polyvinyl pyrrolidone, pectins, starches, gelatin, casein, acrylic acid polymers, polymers of acrylic acid esters, vinyl polymers, vinyl copolymers, polymers of vinyl alcohols, alkoxy polymers, polyethylene oxide polymers, polyethers, and any combination of the above.

In specific embodiments, the mucoadhesive may be a biocompatible polymer, for example polyacrylic acid, that is cross-linked with an acceptable agent to create an insoluble gel. The use of an insoluble gel is desirable since it remains adhered to the mucosal tissue for relatively long periods of time. Cross-linked polyacrylic acid polymers, for example Noveon and Carbomer, may be appropriate for use for three to five days or longer. Noveon and Carbomer-based polymers are weak acids and contain many negatively-charged carboxyl-groups. The multiple negative charges on these polymers promote hydrogen-bonding between the polymers and the negatively charged mucin, a glycoprotein that mediates attachment of mucus to the epithelial lining.

A mucoadhesive polymer may also include acrylic acid polymers (e.g. Carbopol® 940, also known as Carbomer® 940, Carbopol 934P and Carbopol® 980, products of BF Goodrich), methyl vinyl/maleic acid copolymers (e.g. Gantrez® S-97, a product of International Specialty Products), polyvinyl pyrrolidone also known as povidone (e.g. Plasdone® K-90, a product of International Specialty Products). These polymers impart relatively high viscosity at relatively low concentrations. They may therefore be incorporated onto a sensor in amounts ranging from about 0.01% to about 10% by weight relative to the total composition. These viscosity modifying agents further act to improve the film adhesion of the composition to mucous membranes. Carbopol® 980, in certain embodiments, may be 2-3% by weight of the total composition.

The mucoadhesive may be formulated as either a liquid or as a gel. If a liquid formulation is desired, a relatively low concentration (e.g. 0.1-1%) of the mucoadhesive/viscosity modifying agent may be used. If a gel formulation is desired, a higher concentration (e.g. 1.5-4%) of the suitable viscosity modifying/mucoadhesive agent may be incorporated into the polymethacrylate/solvent vehicle for gel formation. The mucoadhesive may be adapted to dissolve upon contact with a solvent.

The mucoadhesive may further comprise excipients e.g. plasticizers, flavorings, sweeteners and/or colorants. Examples of plasticizers include triethyl citrate, polyethylene glycol and glycerin. Such plasticizers may be present in amounts generally ranging from about 1% to about 10% by weight relative to the total composition. For example, glycerine can be present in the amount of 1-5% by weight. Polyethylene glycol and triethyl citrate can be used in the amount of about 5% to about 12%, in certain embodiments.

The indicator layer 12 may include any appropriate indicating element, including chemical, enzymatic, spectrophotometric, fluorescent, or chemiluminescent indicators. In certain embodiments, the indicator layer 12 may include sensing elements, e.g. an emitter and detector pair that may be of any suitable type. For example, the emitter may be one or more light emitting diodes adapted to transmit one or more wavelengths of light in the red to infrared range, and the detector may one or more photodetectors selected to receive light in the range or ranges emitted from the emitter. Alternatively, an emitter may also be a laser diode or a vertical cavity surface emitting laser (VCSEL). An emitter and detector may also include optical fiber sensing elements. An emitter may include a broadband or "white light" source, in which case the detector could include any of a variety of elements for selecting specific wavelengths, for example reflective or refractive elements or interferometers. These kinds of emitters and/or detectors would typically be coupled to the rigid or rigidified sensor via fiber optics. Alternatively, a sensor may sense light detected from the tissue is at a different wavelength from the light emitted into the tissue. Such sensors may be adapted to sense fluorescence, phosphorescence, Raman scattering, Rayleigh scattering and multi-photon events or photoacoustic effects. For pulse oximetry applications using either transmission or reflectance type sensors the oxygen saturation of the patient's arterial blood may be determined using two or more wavelengths of light, most commonly red and near infrared wavelengths. Similarly, in other applications, a tissue water fraction (or other body fluid related metric) or a concentration of one or more biochemical components in an aqueous environment may be measured using two or more wavelengths of light, most commonly near infrared wavelengths between about 1,000 nm to about 2,500 nm. It should be understood that, as used herein, the term "light" may refer to one or more of ultrasound, radio, microwave, millimeter wave, infrared, visible, ultraviolet, gamma ray or X-ray electromagnetic radiation, and may also include any wavelength within the radio, microwave, infrared, visible, ultraviolet, or X-ray spectra.

Alternatively, the indicator layer 12 may include an active ingredient of the indicating element, for example the active ingredient involved in providing the required response signal when exposed to a given concentration of carbon dioxide or other constituents. The active ingredient may be any indicator that is sensitive to the presence of carbon dioxide and that is capable of being calibrated to give a response signal corresponding to a given predetermined concentration of carbon dioxide. The signal may be visual, e.g. a change in color, or electrical. Indicators which provide a color change in a presence of carbon dioxide may include chromogenic pH-sensitive indicators and oxidation/reduction indicators.

A chromogenic pH-sensitive indicator will provide a color change upon exposure to a given concentration of carbon dioxide or other metabolites in the presence of other ingredients of the element which provide the appropriate chemical conditions to induce the required color change. A chromogenic pH-sensitive indicator, e.g. a compound, or mixture of compounds, changes color when there is a change in pH in the surrounding medium. For such an indicator to be capable of giving a determination of carbon dioxide, it is typically used in combination with a suitable base which provides an alkaline solution. The hydroxyl ions or amine residues present in the alkaline solution react chemically with carbon dioxide to produce a carbonate, bicarbonate and/or carbamate moiety. The resulting reaction depletes the hydroxyl ion or amine at the interface and thus lowers the pH at the surface of the component impregnated with the indicating element. The lowering of the pH causes a color change in the indicator.

Chromogenic pH-sensitive indicators according to the present techniques may include metacresol purple, thymol blue, cresol red, phenol red, xylenol blue, a 3:1 mixture of cresol red and thymol blue, bromthymol blue, neutral red, phenolphthalein, rosolic acid, alpha-naphtholphthalein and orange I. Examples of other indicators which may be used include bromcresol purple, bromphenol red, p-nitrophenol, m-nitrophenol, curcumin, quinoline blue, thymolphthalein and mixtures thereof. Suitable bases include sodium carbonate, lithium hydroxide, sodium hydroxide, potassium hydroxide, potassium carbonate, sodium barbitol, tribasic sodium phosphate, dibasic sodium phosphate, potassium acetate, monoethanolamine, diethanolamine and piperidine.

The indicator layer 12 may also include an enzyme-based detection system. For example, one such enzyme may be carbonic anhydrase, which is an enzyme that assists interconversion of carbon dioxide and water into carbonic acid, protons, and bicarbonate ions. As described above, this reaction lowers the pH at the surface of the component impregnated with the indicating element. The lowering of the pH may cause a color change in the indicator. Another such enzyme-based detection system is an enzyme linked immunosorbent assay (ELISA). For example, such an assay may be appropriate when assessing tissue proteins. Thus, the indicator element may include a primary antibody specific for the tissue protein of interest, and a labeled secondary binding ligand or antibody, or a secondary binding ligand or antibody in conjunction with a labeled tertiary antibody or third binding ligand. The label may be an enzyme that will generate color development upon incubating with an appropriate chromogenic substrate. Suitable enzymes include urease, glucose oxidase, alkaline phosphatase or hydrogen peroxidase.

A chemical indicator may be used in conjunction with an electrical or electronic device that is adapted to detect and measure changes in the ambient chemical parameters induced by the presence of critical amounts of carbon dioxide. For example, optical fiber carbon dioxide sensors may be used to convert a change in a chemical indicator to a quantitative measurement of carbon dioxide in the sample. Generally, such sensors operate by directing light of a predetermined wavelength from an external source through the optical fiber to impinge the chemical indicator. The intensity of the emitted fluorescent light returning along the fiber is directly related to the concentration of carbon dioxide in the sample, as a result of the pH-sensitive indicator material present at the fiber tip (i.e., the pH of the indicator solution is directly related to carbon dioxide concentration, as a result of carbonic acid formation). The emitted light is carried by the optical fiber to a device where it is detected and converted electronically to a carbon dioxide concentration value. The sensor may additionally have a reference dye present in the indicator composition. The intensity of the light emitted form the reference dye may be used to compensate, via rationing, the signal obtained from the indicator. Other components may be incorporated into the indicator composition including surfactants, antioxidants and ultraviolet stabilizers may also be present in the indicator composition.

The indicator layer 12 may be formed from any appropriate substrate. For example, the indicator layer 12 may be filter paper, which may be soaked in, dipped in, or otherwise exposed to the appropriate carbon dioxide-sensing compounds. In certain embodiments, the filter paper may be dipped into a solution containing the indicating compounds on only one side. The indicator layer 12 may also be polysulfone, polypropylene, or other polymer substrates. The indicator layer 12 may be a thin film, or a thicker substrate. A thicker substrate may lead to a slower response time, which may be advantageous in situations in which a sensor is monitoring carbon dioxide levels over a longer period of time. Additionally, the indicator layer 12 may have pores of a variety of sizes.

Figure 2:
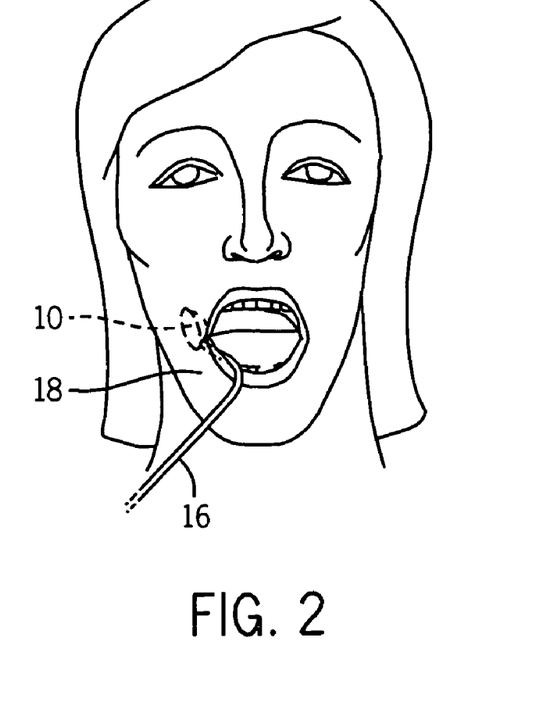
FIG. 2 illustrates a perspective view of a patient using a sensor for detection of a physiological constituent according to the present invention.

In specific embodiments, it may be advantageous to provide a sensor for use on buccal or sublingual tissue that is easily reached by the patient or a healthcare worker. For example, FIG. 2 illustrates the placement of a sensor with a mucoadhesive on a buccal surface in order to assess a tissue gas, for example carbon dioxide, in the tissue, blood or interstitial fluid. Specifically, FIG. 2 shows an embodiment of a sensor 10 including an output cable 16 that is adapted to provide an electrical feedback. Alternatively, reference number 16 may represent a string, cord, or tether that facilitates removal of the sensor 10. In another embodiment, reference number 16 may represent a gas collection tube. In such an embodiment, the sensor 10 may collect tissue gases in a chamber. The collected gases may then diffuse through a tube connected to the collection chamber, and the gases may then be further assessed and/or measured by sensing elements not directly applied to the patient. The sensor 10 may be suitably sized and shaped such that a patient may easily close his or her mouth around the sensor with minimal discomfort.

The sensor 10 is secured to the buccal tissue 18 such that the area covered by the sensor 10 is substantially sealed to prevent air flow out of the sensor 10, thus preventing carbon dioxide at the sensor placement site from dissipating into the airstream, which may lead to inaccurate measurements. Further, the sensor's 10 tissue seal may also prevent respiratory gases or oral fluids from entering the sensor 10. Generally, the sensor 10 may be suitably sized and shaped to allow the sensor 10 to be positioned flush against the buccal tissue 18.

Figure 3:
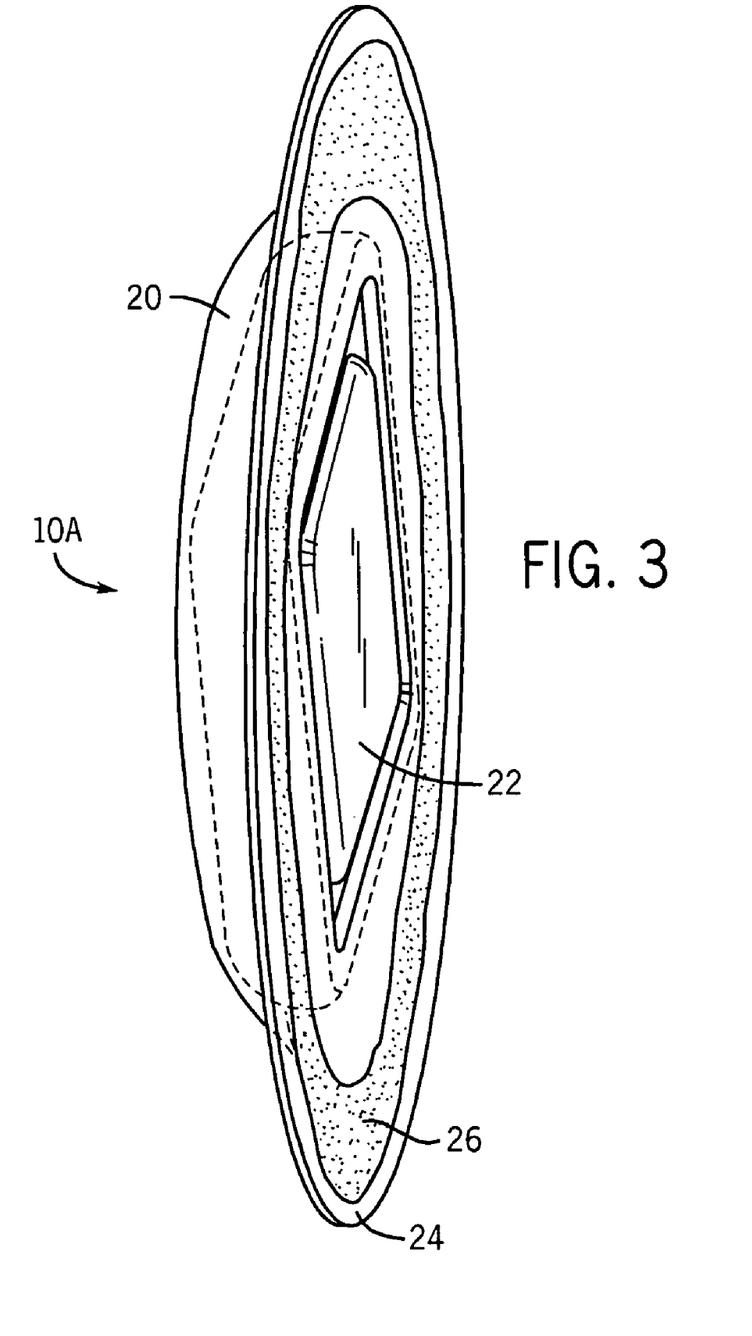
FIG. 3 illustrates a side perspective view of a sensor for detection of tissue or blood constituents with a mucoadhesive region according to the present invention.

FIG. 3 is a perspective view of an exemplary sensor 10A. The sensor 10A includes a housing 20 surrounding an indicator layer 22. The housing is formed to provide a surface 24 that is suitably shaped to be secured against a mucosal tissue. Mucoadhesive 26 is disposed on the surface 24. The mucoadhesive 26 may include a substrate holder, for example a paper or foam. In such an embodiment, the paper or foam is soaked in or otherwise impregnated with the mucoadhesive 26 in the form of a gel or liquid.

The mucoadhesive 26 is disposed on the sensor 10A in a ring substantially surrounding the indicator layer 22. Thus, when the sensor 10A is applied to tissue, the mucoadhesive 26 adheres in a region of tissue adjacent to the indicator layer 22, such that the indicator layer 22 is in direct contact with the mucous membrane. In certain embodiments, the mucoadhesive 26 is permeable to the tissue gases being measured. In such an embodiment, the mucoadhesive 26 may be applied directly to the sensor placement site on the tissue by a healthcare worker. Thus, the mucoadhesive 26 would be disposed between the mucous membrane and the indicator layer 22, and the tissue carbon dioxide or other constituents would perfuse through the mucoadhesive 26 before reaching the indicator layer 22. Such an arrangement may be advantageous if the mucoadhesive 26 must be freshly prepared prior to use, and cannot be stored with the sensor 10A.

In other embodiments (not shown), it may be advantageous to package the sensor in foil or other protective materials in order to protect the mucoadhesive 26 prior to use, and prevent drying out or oxidation of the mucoadhesive 26 layer.

The housing 20 may be any suitable material that is generally suited to the aqueous environment of the mucous membrane, for example plastic. In certain embodiments, the housing 20 may be may be any suitable optically transparent material that allows for viewing of the indicator layer 22 beneath. Exemplary materials include transparent polymers, for example polypropylene or polyethylene terephthalate (PET). In other embodiments, the housing 20 may be an opaque material with a transparent window that allows viewing of the indicator layer 22. However, in other embodiments in which the sensor 10A is adapted to provide electrical feedback to a monitor, the sensor 10A may or may not include a mechanism for viewing a color change of the indicator layer 20.

Figure 4:
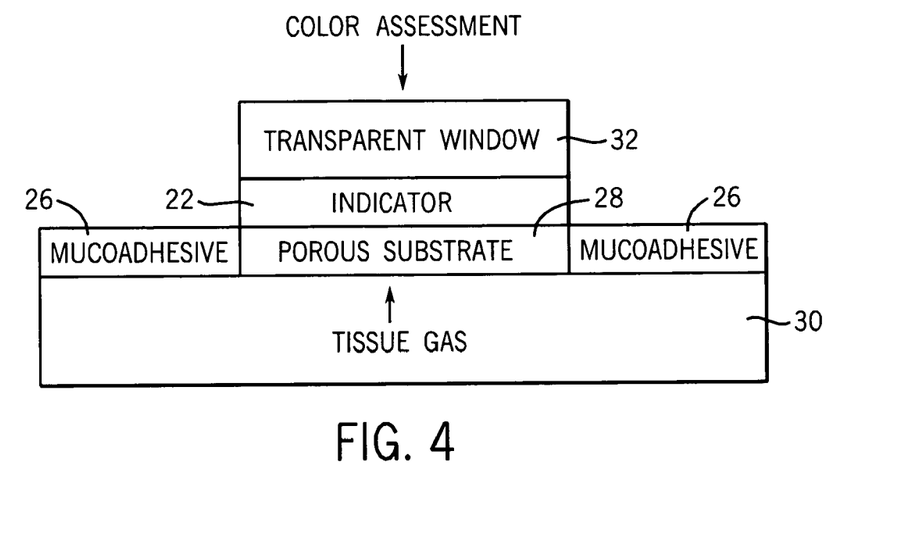
FIG. 4 illustrates a schematic cross-sectional view of the sensor of FIG. 3.

FIG. 4 is a schematic view of the exemplary sensor 10A that includes a permeable substrate 28 disposed in the tissue-contacting side of the indicator layer 22. A permeable substrate 28 may be advantageous in providing rigidity and support to the sensor assembly 10A. Suitable materials for a permeable substrate 28 include, but are not limited to paper, plastics, or woven materials. Carbon dioxide or other constituents 30 at the surface of the mucosal tissue contacts the permeable substrate 28 when the sensor assembly is applied to a mucosal surface. The substrate 28 is permeable to carbon dioxide or other constituents 30, which diffuses to contact the indicator layer 22. A transparent window 32 allows viewing of the response, for example a change in color of the indicator layer 22.

Figure 5:
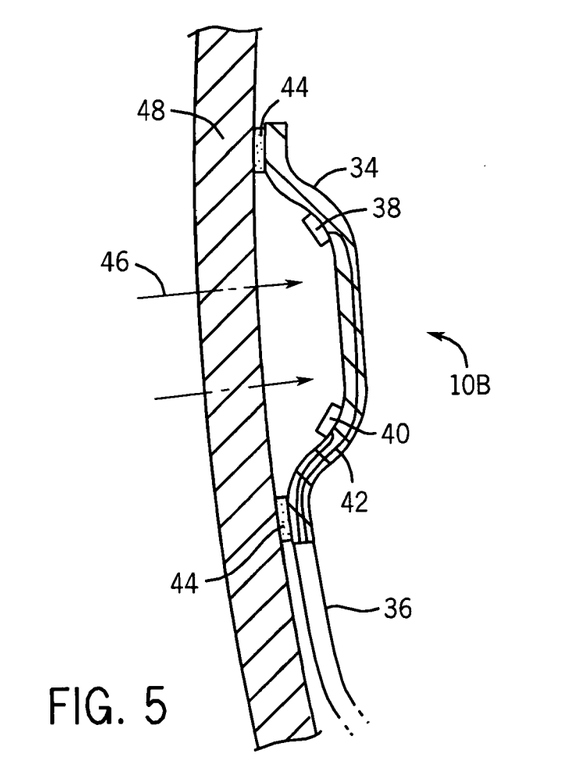
FIG. 5 illustrates cross-sectional view of a sensor for detection of tissue or blood constituents with a collection chamber according to the present invention

FIG. 5 is an alternate embodiment of a tissue constituent sensor 10B in which the sensor includes an electrical indicator. A housing 34 is adhered to the mucosal tissue 48 by a mucoadhesive 44. The housing 34, once adhered, forms a collection chamber that traps tissue gas 46 that diffuses through the mucosal tissue 48. The trapped tissue gas 46 may then be irradiated by an emitter 38, and the emitted light that passes through the tissue gas 46 is detected by a detector 40. The emitter 38 and the detector 40 are electrically coupled to a cable 36 by a pair of wires 42. The wavelength of the light emitted by the emitter 38 and the detection range of the detector 40 may be selected to detect a wide range of tissue gases 46, including carbon dioxide.

The housing 34 may be formed from polypropylene, polyethylene, polysulfone or similar polymers. Generally, the housing should be relatively impermeable to tissue gases, such that the sensor 10B may collect tissue gases 46 for a sufficient period of time to allow for detection and measurement. Hence, it may be advantageous to coat the sensor 10B with additional sealants to prevent leakage of the tissue gases 46.

In certain embodiments, the emitter 38 may be an infrared light source, for example an incandescent broad band lamp, (available from Oshino Lamps). In such an embodiment, the sensor may also include an infrared detector 40, for example a lead selenide detector (available from OptoElectronics). The emitter may also include a filter, for example a 4.26 micron wavelength filter. Such a filter may be appropriate for use in an embodiment where carbon dioxide is measured.

In some embodiments, the sensor 10B is arranged to operate in transmission mode, and casings for the emitter and detector may be formed in the housing 34 on opposite sides of the sensor 10B. In an alternate embodiment, the emitter 38 and the detector 40 may be arranged to operate in reflectance mode (not shown), and can be located on the same side of sensor 10B. In such an embodiment (not shown), a mirror may be placed on the opposite side of the housing 34 to reflect the radiation emitted from the emitter 38 back to the detector 40.

Figure 6:
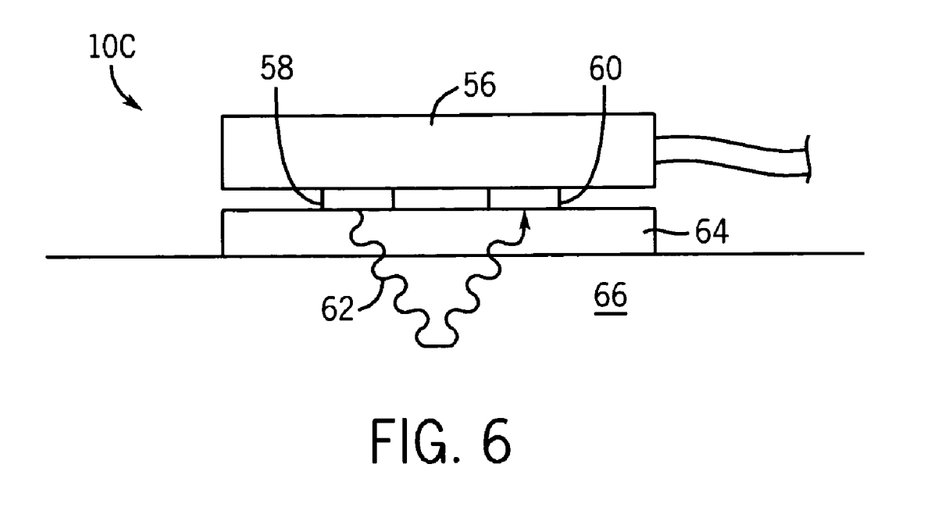
FIG. 6 illustrates cross-sectional view of an exemplary pulse oximetry sensor adhered to the mucous membrane according to the present invention.

FIG. 6 illustrates an exemplary reflectance pulse oximetry sensor 10C. The sensor 10C has an indicator layer that includes a sensor body 56 and an emitter 58 and a detector 60 that generally lie side-by-side. The sensor 10C is adhered to the mucous membrane 66 with a mocoadhesive 64. The sensor 10C is arranged such that the emitter 58 emits light, represented by arrow 62 that is absorbed and/or scattered back to the detector 60. The emitter 58 and the detector 60 may be disposed on the sensor body 56, which may be made of any suitable material, for example plastic, foam, woven material, or any water-resistant material. Alternatively, the emitter 58 and the detector 60 may be remotely located and optically coupled to the sensor 10C using optical fibers. In an alternative embodiment (not shown), the sensor 10C may be a transmission type sensor. Transmission type sensors include an emitter 58 and detector 60 that are typically placed on opposing sides of the sensor site. Thus, part of the sensor may be adhered to the mucous membrane of the cheek with a mucoadhesive 64 and a part of the sensor may be adhered to the exterior portion of the cheek with other suitable adhesives, such that the emitter 58 and the detector 60 are positioned on opposite sides of the cheek. In other words, the sensor 10C is positioned so that the emitter 58 is located on the interior of patient's mouth and the detector 60 is located 180° opposite the emitter 58 on the exterior of the patients mouth. In such an arrangement, a conformable sensor body 56 may connect the emitter 58 and the detector 60. In each of the embodiments discussed herein, it should be understood that the locations of the emitter 58 and the detector 60 may be exchanged. In either arrangement, the sensor 10C will perform in substantially the same manner.

Figure 7:
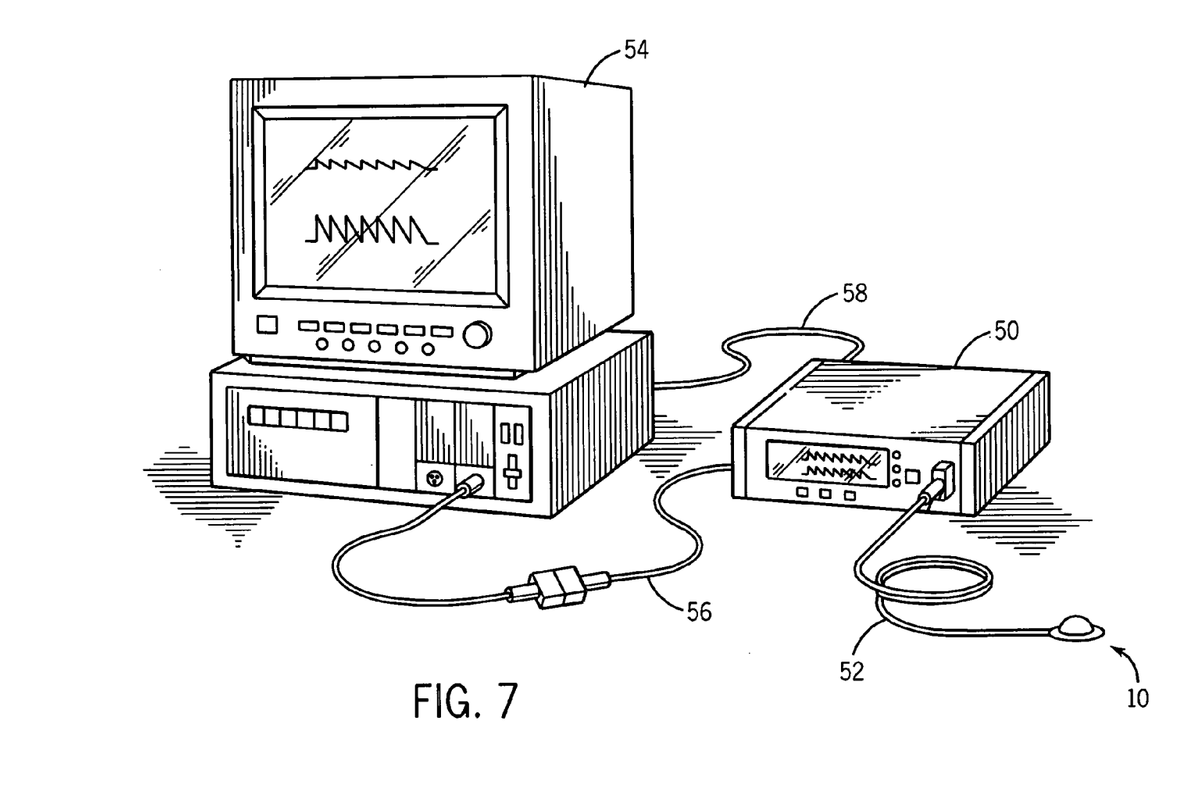
FIG. 7 illustrates a physiological constituent detection system coupled to a multi-parameter patient monitor and a sensor according to embodiments of the present invention.

The exemplary sensors described herein, illustrated here generically as a sensor 10, may be coupled to a monitor 50, for example a carbon dioxide monitor or a pulse oximetry monitor, that may display the concentration of a physiological constituent in the patient sample (e.g. mucosal tissue or blood) as shown in FIG. 7. It should be appreciated that the cable 52 of the sensor 10 may be coupled to the monitor 50 or it may be coupled to a transmission device (not shown) to facilitate wireless transmission between the sensor 10 and the monitor 50. The monitor 50 may be any suitable carbon dioxide monitor, for example those available from Nellcor Puritan Bennett Inc. Furthermore, to upgrade conventional carbon dioxide detection provided by the monitor 50 to provide additional functions, the monitor 50 may be coupled to a multi-parameter patient monitor 54 via a cable 56 connected to a sensor input port or via a cable 58 connected to a digital communication port.

While the invention may be susceptible to various modifications and alternative forms, specific embodiments have been shown by way of example in the drawings and have been described in detail herein. However, it should be understood that the invention is not intended to be limited to the particular forms disclosed. Indeed, the present techniques may not only be applied to measurements of carbon dioxide, but these techniques may also be utilized for the measurement and/or analysis of other blood or tissue constituents. Rather, the invention is to cover all modifications, equivalents, and alternatives falling within the spirit and scope of the invention as defined by the following appended claims. It will be appreciated by those working in the art that sensors fabricated using the presently disclosed and claimed techniques may be used in a wide variety of contexts. That is, while the invention has primarily been described in conjunction with the measurement of physiological constituents in the blood or tissue, the sensors fabricated using the present method may be used to evaluate any number of sample types in a variety of industries, including fermentation technology, cell culture, and other biotechnology applications.

What is claimed is:

1. A method comprising:
securing a sensor to a mucosal tissue with a mucoadhesive, wherein the sensor comprises an indicator adapted to provide feedback related to a physiological constituent, and wherein the mucoadhesive is disposed on a tissue-contacting side of the indicator, wherein the indicator comprises an emitter and a detector disposed on the tissue-contacting surface and wherein the mucoadhesive is in direct contact with the emitter and detector.

2. The method, as set forth in claim 1, wherein the physiological constituent comprises at least one of a tissue or blood constituent.

3. The method, as set forth in claim 1, wherein the physiological constituent comprises at least one of a metabolic trace gases or an anesthetic gas.

4. The sensor, as set forth in claim 1, wherein the physiological constituent comprises at least one tissue metabolite.

5. The sensor, as set forth in claim 1, wherein the physiological constituent comprises at least one of carboxyhemoglobin or methemoglobin.

6. The method, as set forth in claim 1, wherein the sensor comprises at least one of a pulse oximetry sensor or a carbon dioxide sensor.

7. The method, as set forth in claim 6, comprising assessing the presence of carbon dioxide by viewing an indicator through an optically transparent layer.

8. The method, as set forth in claim 6, comprising assessing the presence of carbon dioxide by providing an electrical feedback.

9. The method, as set forth in claim 1, comprising detaching the sensor by applying a solvent to the mucosal tissue.

* * * * *